(12) United States Patent
Chernyak

(10) Patent No.: US 7,083,609 B2
(45) Date of Patent: Aug. 1, 2006

(54) CORNEAL TOPOGRAPHY-BASED TARGET WARPING

(75) Inventor: Dimitri Chernyak, Los Gatos, CA (US)

(73) Assignee: VISX, Incorporated, Santa Clara, CA (US)

(*) Notice: Subject to any disclaimer, the term of this patent is extended or adjusted under 35 U.S.C. 154(b) by 291 days.

(21) Appl. No.: 10/460,060

(22) Filed: Jun. 11, 2003

(65) Prior Publication Data

US 2004/0019346 A1 Jan. 29, 2004

Related U.S. Application Data

(60) Provisional application No. 60/389,090, filed on Jun. 13, 2002.

(51) Int. Cl.
*A61F 9/008* (2006.01)

(52) U.S. Cl. ............................. 606/5; 128/898; 606/4
(58) Field of Classification Search .............. 606/4–5; 128/898

See application file for complete search history.

(56) References Cited

U.S. PATENT DOCUMENTS

| | | | |
|---|---|---|---|
| 4,540,254 A | 9/1985 | Humphrey | |
| 4,665,913 A | 5/1987 | L'Esperance | |
| 4,761,071 A | 8/1988 | Baron | |
| 4,848,340 A * | 7/1989 | Bille et al. ............ | 606/4 |
| 4,995,716 A | 2/1991 | Warnicki et al. | |
| 5,144,630 A | 9/1992 | Lin | |
| 5,163,934 A | 11/1992 | Munnerlyn | |
| 5,219,344 A * | 6/1993 | Yoder, Jr. ............ | 606/5 |
| 5,406,342 A | 4/1995 | Jongsma | |
| 5,491,524 A | 2/1996 | Hellmuth et al. | |
| 5,646,791 A | 7/1997 | Glockler | |
| 5,683,379 A | 11/1997 | Hohla | |
| 5,713,892 A | 2/1998 | Shimmick | |
| 5,742,626 A | 4/1998 | Mead et al. | |
| 5,777,719 A | 7/1998 | Williams et al. | |
| 5,843,070 A | 12/1998 | Cambier et al. | |
| 5,912,775 A | 6/1999 | Glockler | |
| 5,912,779 A | 6/1999 | Llewellyn et al. | |
| 6,042,012 A | 3/2000 | Olmstead et al. | |
| 6,095,651 A | 8/2000 | Williams et al. | |
| 6,116,738 A | 9/2000 | Rorabaugh | |
| 6,129,722 A | 10/2000 | Ruiz | |
| 6,199,986 B1 | 3/2001 | Williams et al. | |
| 6,203,539 B1 | 3/2001 | Shimmick et al. | |
| 6,217,570 B1 * | 4/2001 | Nevyas ............ | 606/5 |
| 6,217,915 B1 | 4/2001 | Luchansky et al. | |
| 6,245,059 B1 | 6/2001 | Clapham | |

(Continued)

OTHER PUBLICATIONS

Excimer Laser Surgery by Thompson et al., Igaku–Shoin Medical Publishers, 1993.*

Borsuztky et al., "*Tunable UV Radiation at Short Wavelengths (188–240 nm) Generated by Sum Frequency Mixing in Lithium Borate*", Appl. Phys. 61:529–532 (1995).

Primary Examiner—Henry M Johnson, III
(74) Attorney, Agent, or Firm—Townsend and Townsend and Crew LLP; Mark D. Barrish

(57) ABSTRACT

Systems and methods for treating a tissue of an eye with a laser beam include at least one processor that determines angles between a curved surface and a laser beam, controlling an ablative treatment in response to the angles. Angles between a surface of a cornea and a laser beam may be mapped over a treatment area. A mapped area may include an apex of a cornea displaced from a center of a pupil in an eye. Ablation properties may be determined locally in response to the incident angle of a laser beam with respect to a local slope of a tissue surface. The treatment area may be ablated using local ablation properties to form a desired surface shape.

7 Claims, 18 Drawing Sheets

U.S. PATENT DOCUMENTS

| | | |
|---|---|---|
| 6,271,914 B1 | 8/2001 | Frey et al. |
| 6,280,435 B1 | 8/2001 | Odrich et al. |
| 6,302,876 B1 | 10/2001 | Shimmick et al. |
| 6,315,413 B1 | 11/2001 | Shimmick et al. |
| 6,319,247 B1 | 11/2001 | Hofer et al. |
| 6,331,177 B1 | 12/2001 | Munnerlyn et al. |
| 6,396,069 B1 | 5/2002 | MacPherson et al. |
| 6,467,907 B1 * | 10/2002 | Fujieda et al. ............... 351/212 |
| 6,530,917 B1 * | 3/2003 | Seiler et al. .................... 606/5 |
| 6,572,606 B1 * | 6/2003 | Kliewer et al. ................. 606/5 |
| 6,730,074 B1 * | 5/2004 | Bille et al. ..................... 606/5 |
| 2002/0049431 A1 * | 4/2002 | Smith et al. .................... 606/5 |
| 2003/0105457 A1 * | 6/2003 | Mrochen et al. ................ 606/5 |

\* cited by examiner

CORNEAL TOPOGRAPHY-BASED TARGET WARPING

CROSS-REFERENCE TO RELATED APPLICATION

This is a non-provisional patent application which claims priority from U.S. Provisional Patent Application No. 60/389,090 filed Jun. 13, 2002, the full disclosure of which is incorporated herein by reference.

BACKGROUND OF THE INVENTION

The present invention is generally related to correction of refractive errors and aberrations of the eye. The invention provides devices, systems, and methods for measurement and correction of optical errors of optical systems, and is particularly well suited for correcting refractive optical aberrations of the eye.

Known laser eye surgery procedures generally employ an ultraviolet or infrared laser to remove a microscopic layer of stromal tissue from the cornea of the eye. Examples of laser eye surgery procedures include photorefractive keratectomy (PRK), phototherapeutic keratectomy (PTK), laser assisted in situ keratomileusis (LASIK), laser epithelial keratomileusis (LASEK), and the like. A laser typically removes a selected shape of a corneal tissue, often to correct refractive errors of an eye. Ultraviolet laser ablation results in photodecomposition of a corneal tissue, but generally does not cause significant thermal damage to adjacent and underlying tissues of an eye. Irradiated molecules are broken into smaller volatile fragments photochemically, directly breaking intermolecular bonds.

Laser ablation procedures can remove a targeted amount stroma of a cornea to change a cornea's contour for varying purposes, such as for correcting myopia, hyperopia, astigmatism, and the like. Control over a distribution of ablation energy across a cornea may be provided by a variety of systems and methods, including use of ablatable masks, fixed and moveable apertures, controlled scanning systems, eye movement tracking mechanisms, and the like. In known systems, a laser beam often comprises a series of discrete pulses of laser light energy, with a total shape and amount of tissue removed being determined by a shape, size, location, and/or number of laser energy pulses impinging on a cornea. A variety of algorithms may be used to calculate the pattern of laser pulses used to reshape a cornea so as to correct a refractive error of an eye. Known systems make use of a variety of forms of lasers and laser energy to effect a correction, including infrared lasers, ultraviolet lasers, femtosecond lasers, wavelength multiplied solid-state lasers, and the like. Alternative vision correction techniques make use of radial incisions in a cornea, intraocular lenses, removable corneal support structures, and the like.

Known corneal correction treatment methods have generally been successful in correcting standard vision errors, such as myopia, hyperopia, astigmatism, and the like. By customizing an ablation pattern based on wavefront measurements, it may be possible to correct minor aberrations so as to reliably and repeatedly provide visual acuity greater than 20/20. Such detailed corrections will benefit from an extremely accurate ablation of tissue.

Known methods for calculation of a customized ablation pattern using wavefront sensor data generally involves mathematically modeling a surface of the cornea using expansion series techniques. More specifically, Zernike polynomials have been employed to model the corneal surface and refractive aberrations of the eye. Coefficients of a Zernike polynomial are derived through known fitting techniques, and an optical correction procedure is then determined using a shape indicated by a mathematical series expansion model.

Work in connection with the present invention suggests that the known methodology for determining laser ablation treatments based on wavefront sensor data and spectacles may be less than ideal. The known techniques typically do not take into account a detailed ablative interaction of a laser beam with a detailed anatomy of a tissue surface of an eye.

In light of the above, it would be desirable to provide improved ablation techniques, particularly for refractive correction purposes.

BRIEF SUMMARY OF THE INVENTION

The present invention provides systems and methods for treating a tissue of an eye with a laser beam. A local ablation property is determined based at least in part on an angle of an incident laser beam with a surface of a tissue. A treatment area is ablated using local ablation properties.

In a first aspect, the invention comprises a method of treating a cornea of a patient's eye with a laser beam. Angles between a surface of a cornea and a laser beam are mapped over a treatment area. Ablation properties are determined locally across a treatment area in response to mapped angles so as to formulate a treatment plan using local ablation properties. A treatment area is ablated according to the treatment plan to form a desired shape in a surface.

In some embodiments, an angle of a laser beam may be substantially parallel to an optical axis of an eye. A mapped area includes an apex of a cornea and an apex of a cornea is displaced from a center of a pupil of an eye. A desired shape has a center, and a center of a desired shape may be aligned with a center of a pupil of an eye. A virtual shape may be adjusted from a first virtual shape to a second virtual shape. A first virtual shape may represent a depth of material removed from an area to form a desired shape. A second virtual shape may be formed from a first virtual shape in response to the mapped angles. In an embodiment, a depth of a second virtual shape may be greater than a depth of a first virtual shape. In another embodiment, a depth of a second virtual shape may be less than a depth of a first virtual shape. A desired shape may be based at least in part on a result of measurement selected from a group consisting of an aberration measurement of an eye, a refractive measurement of an eye, and a topography measurement of an eye.

In another aspect, the invention comprises a system for treating a cornea of a patient's eye with a laser beam. The system includes a laser emitting a beam of an ablative light energy and at least one processor. At least one processor has a computer program mapping angles between a surface of a cornea and a laser beam. At least one processor determines local ablation properties of a cornea in response to mapped angles. At least one processor has a computer program controlling an ablative treatment in response to local ablation properties. A treatment forms a desired shape in a surface.

In some embodiments, an angle of a laser beam may be substantially parallel to an optical axis of an eye. A mapped area may include an apex of a cornea, and an apex of a cornea may be displaced from a center of a pupil of an eye. A desired shape may have a center, and a center of a desired shape may be aligned with a center of a pupil of an eye. At least one processor having a computer program may include a first virtual shape and a second virtual shape. A first virtual shape may represent a depth of material removed from an area to form a desired shape, and a second virtual shape may be formed from a first virtual shape in response to mapped angles. In an embodiment, a depth of a second virtual shape may be greater than a depth of a first virtual shape. In another embodiment, a depth of a second virtual shape may be less than a depth of a first virtual shape. A desired shape may be based at least in part on a result of measurement selected from a group consisting of an aberration measurement of an eye, a refractive measurement of the eye, and a topography measurement of the eye.

In a further aspect, the invention comprises a system for treating a cornea of an eye with a laser beam. A system includes a laser emitting a beam of an ablative light energy and at least one processor having a computer program. At least one processor determines angles between a curved surface and a laser beam. At least one processor has a computer program controlling an ablative treatment in response to angles between a curved surface and a laser beam. A treatment forms a desired shape in a surface.

In specific embodiments, at least one processor determines local ablation properties of a cornea in response to angles between a curved surface and a laser beam. An angle of a laser beam is substantially parallel to an optical axis of an eye. A mapped area includes an apex of a cornea and an apex of a cornea is displaced from a center of a pupil of an eye. A desired shape has a center, and a center of a desired shape is aligned with a center of a pupil of an eye. At least one processor has a computer program including a first virtual shape and a second virtual shape. A first virtual shape represents a depth of material removed from an area to form a desired shape. A second virtual shape is formed from a first virtual shape in response to mapped angles. In an embodiment, a depth of a second virtual shape is greater than a depth of a first virtual shape. In another embodiment, a depth of a second virtual shape is less than a depth of a first virtual shape. A desired shape is based at least in part on a result of a measurement selected from a group consisting of an aberration measurement of an eye, a refractive measurement of the eye, and a topography measurement of an eye.

DETAILED DESCRIPTION OF THE INVENTION

Figure 1:
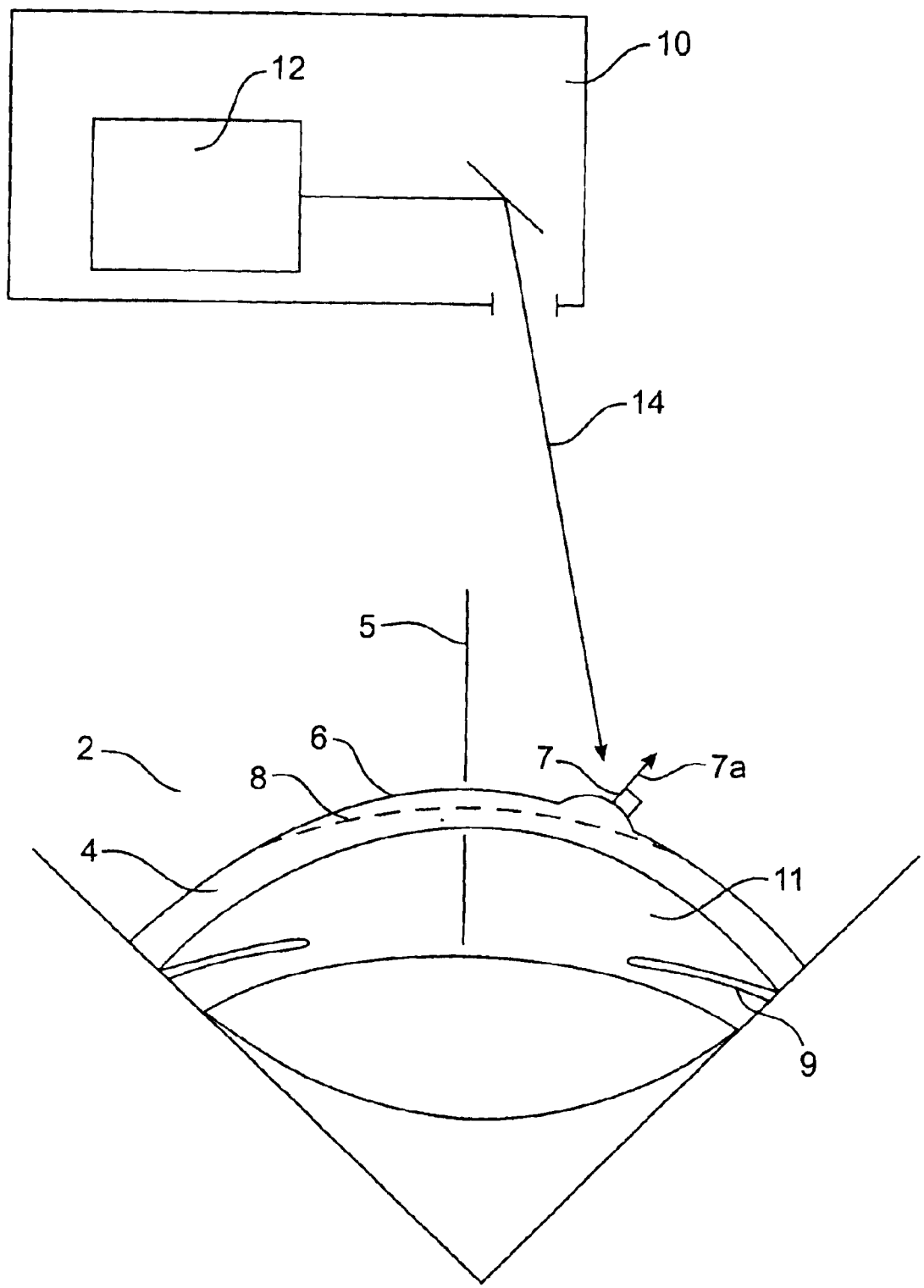
FIG. 1 illustrates a laser system ablating a tissue surface in accord with an embodiment of the present invention.

The present invention is particularly useful for enhancing the accuracy and efficacy of laser eye surgical procedures, such as photorefractive keratectomy (PRK), phototherapeutic keratectomy (PTK), laser assisted in situ keratomileusis (LASIK), laser epithelial keratomileusis (LASEK) and the like. Preferably, the present invention can provide enhanced optical accuracy of refractive procedures by improving a corneal ablation of a refractive treatment program. Hence, while the system and methods of the present invention are described primarily in a context of a laser eye surgery system, it should be understood techniques of the present invention may be adapted for use in alternative eye treatment procedures and systems such as spectacle lenses, intraocular lenses, contact lenses, corneal ring implants, collagenous corneal tissue thermal remodeling, and the like.

The techniques of the present invention can be readily adapted for use with existing laser systems, wavefront sensors, corneal topography systems, phoropters and other optical measurement devices. By providing a more detailed (and hence, less prone to alignment and other errors) methodology for determining a laser treatment plan, the present invention may facilitate sculpting of the cornea so that treated eyes regularly exceed a normal 20/20 threshold of desired vision.

As used herein an "optical tissue surface" may encompass a theoretical tissue surface derived from an optical measurement of light refraction of an eye (exemplified by wavefront sensor data and manifest refraction data), an actual tissue surface, and/or a tissue surface formed for purposes of treatment (for example, by incising corneal tissues so as to allow a flap of the corneal epithelium to be displaced and expose the underlying stroma during a LASIK procedure).

Systems and methods for measuring a refractive error of an eye such as spherical defocus and cylindrical astigmatism having an axis are well known in the optometric and ophthalmic fields. Examples of measurements of a refractive error of an eye are manifest, cycloplegic, and retinoscopic refraction. U.S. Pat. No. 5,163,934, the full disclosure of which is incorporated herein by reference, describes a shape of tissue to be removed from a cornea of an eye to correct a refractive error of an eye. Systems and methods for measuring a corneal topography of an eye are well known in the optometric and ophthalmic fields. For example, U.S. Pat. Nos. 4,761,071, 4,995,716, 5,406,342, 6,396,069, 6,116,738, 4,540,254 and 5,491,524, the full disclosures of which are incorporated herein by reference, describe systems and methods for measuring a corneal topography of an eye. Systems and methods for determining an ablation location and shape using corneal topography are described in U.S. Pat. Nos. 6,245,059, 6,129,722 and 5,843,070, the full disclosures of which are incorporated herein by reference.

Wavefront sensors will typically measure aberrations and other optical characteristics of an entire optical tissue system. Data from such a wavefront sensor may be used to generate an optical tissue surface from an array of optical gradients. In some instances, an optical tissue surface may be referred to as a wavefront elevation map. An optical tissue surface may not precisely match an actual tissue surface. For example, optical gradients will show effects of aberrations, which are actually located throughout an ocular tissue system. Nonetheless, corrections imposed on an optical tissue surface so as to correct aberrations derived from gradients should correct an optical tissue system. Systems and methods for measuring and correcting aberrations of an optical tissue surface of eye based on wavefront elevation maps are described in U.S. Pat. Nos. 5,777,719, 6,042,012, 6,095,651, 6,199,986, 6,271,914 and 6,217,915, the full disclosures of which are incorporated herein by reference.

In correcting an optical tissue surface of an eye, a shape of tissue to be removed is typically determined prior to ablation. A predetermined shape is often the result of a combination of refractive error, wavefront sensor and topography measurements as described above.

A laser ablating a surface of an eye is illustrated in FIG. 1 in accordance with an embodiment of the invention. An eye 2 is illustrated in cross section as being ablated by a laser system 10 having a laser 12 emitting a beam 14 of an ablative light energy. An eye 2 has a cornea 4. An eye 2 has a pupil 11 formed in an iris 9. A cornea 4 has a surface 6. A surface 6 of a cornea 4 has a local surface angle 7. A local surface angle 7 is preferably a surface normal vector 7a, but can be any representation of a local slope of surface 6. An eye 2 has at least one axis, for example an optical axis 5. An optical axis 5 of an eye 2 is aligned with a system 10. A desired predetermined shape 8 is formed in a surface 6 with a series of pulses of a laser beam 14 of an ablative light energy.

As tissue ablates from surface 6 to form predetermined a shape 8, an amount of tissue ablated with each pulse of laser beam 14 varies with an angle between a surface angle 7 and a laser beam 14. Typically, an amount of tissue removed with a pulse of a laser beam 14 will decrease as a local surface having an angle 7 faces away from a laser beam 14. By determining a local amount of ablation from a local angle between a local surface angle and a local angle of laser beam incident on the local surface, a treatment program will more accurately calculate a distribution pattern of a series of pulses to form a desired predetermined shape 8.

Figure 1A:
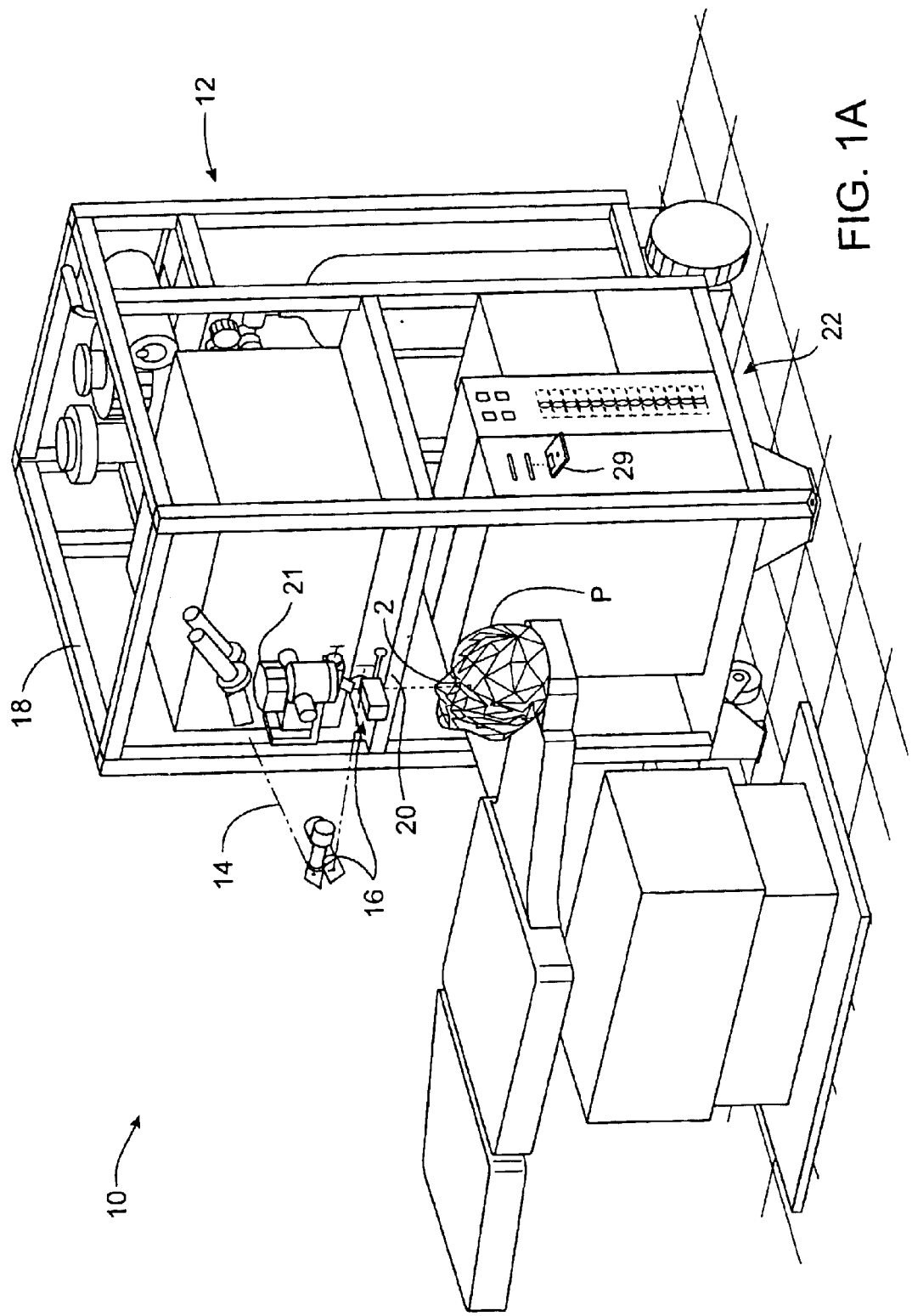
FIG. 1A is a perspective view of a laser ablation system for incorporating the present invention.

Referring now to FIG. 1A, a laser eye surgery system 10 for incorporating the present invention includes a laser 12 that produces a laser beam 14. Laser delivery optics 16 are in a path of laser beam 14. Delivery optics 16 direct laser beam 14 to an eye of a patient P. A delivery optics support structure (not shown here for clarity) extends from a frame 18 supporting laser 12. An input device 20 is used to align laser system 10 in relation to an eye of a patient P. A microscope 21 is mounted on the delivery optics support structure, the microscope often being used to image a cornea of an eye. In various embodiments, a laser eye surgery system 10 includes at least some portions of a Star S3 Active Trak™ Excimer Laser System available from VISX, INCORPORATED of Santa Clara, Calif.

While an input device 20 is here schematically illustrated as a joystick, a variety of input components may be used. Suitable input components may include trackballs, touch screens, or a wide variety of alternative pointing devices. Still further alternative input components include keypads, data transmission mechanisms such as an Ethernet, intranet, Internet, a modem, or the like.

A laser 12 generally comprises an excimer laser and ideally comprises an argon-fluoride laser producing pulses of laser light having a wavelength of approximately 193 nm. A pulse of laser light typically has a fixed pulse duration having a full width half maximum (FWHM) of about 15 nano seconds during a treatment. Laser 12 is preferably designed to provide a feedback stabilized fluence at the patient's eye, delivered via delivery optics 16. The present invention may also be useful with alternative sources of ultraviolet or infrared radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193–215 nm) such as those described in U.S. Pat. Nos. 5,144,630 and 5,742,626, Borsuztky et al., "*Tunable UV Radiation at Short Wavelengths (188–240 nm) Generated by Sum Frequency Mixing in Lithium Borate*", *Appl. Phys.* 61:529–532 (1995), and the like. Laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to an eye of patient P under direction of a processor 22. Processor 22 will often selectively adjust laser beam 14 to expose portions of the cornea to pulses of laser energy so as to effect a predetermined sculpting of a cornea and alter refractive characteristics of an eye. In many embodiments, both laser 14 and a laser delivery optical system 16 will be under computer control of processor 22 to effect a desired laser sculpting process, with processor 22 effecting (and optionally modifying) a pattern of laser pulses. A pattern of pulses may by summarized in a treatment table listing of machine readable data of a tangible media 29. A treatment table may be adjusted according to feedback input into processor 22 from an automated image analysis system (manually input into processor 22 by a system operator) in response to feedback data provided from an ablation monitoring system feedback system. Such feedback might be provided by integrating a wavefront measurement system described below with a laser treatment system 10, and processor 22 may continue and/or terminate a sculpting treatment in response to feedback, and may optionally also modify a planned sculpting based at least in part on feedback.

Laser beam 14 may be adjusted to produce a desired sculpting using a variety of alternative mechanisms. A laser beam 14 may be selectively limited using one or more variable apertures. An exemplary variable aperture system having a variable iris and a variable width slit is described in U.S. Pat. No. 5,713,892, the full disclosure of which is incorporated herein by reference. A laser beam may also be tailored by varying a size and offset of a laser spot from an axis of an eye, as described in U.S. Pat. No. 5,683,379, and as also described in co-pending U.S. patent application Ser. Nos. 08/968,380, filed Nov. 12, 1997; and 09/274,999 filed Mar. 22, 1999, the full disclosures of which are incorporated herein by reference.

Still further alternatives are possible, including scanning a laser beam over a surface of an eye and controlling a number of pulses and/or dwell time at each location, as described, for example, by U.S. Pat. No. 4,665,913 (the full disclosure of which is incorporated herein by reference); using masks in an optical path of laser beam 14 which ablate to vary a profile of a beam incident on a cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea as described in U.S. Pat. Nos. 6,319,247; 6,280,435; and 6,203,539, the full disclosures of which are incorporated herein by reference; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. Nos. 5,646,791 and 5,912,779 the full disclosures of which are incorporated herein by reference. An ablation effluent evacuator/filter, and other ancillary components of the laser surgery system which are not necessary to an understanding of the invention, which may be optionally employed, need not be described in detail for an understanding of the present invention.

Processor 22 may comprise (or interface with) a conventional PC system including standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any methods of the present invention. Tangible storage media 29 may comprise a floppy disk, an optical disk, a data tape, a volatile or non-volatile memory, or the like, and a processor 22 will include memory boards and other standard components of modern computer systems for storing and executing a computer program code. Tangible storage media 29 may optionally embody wavefront sensor data, wavefront gradients, a wavefront elevation map, a treatment map, a corneal topography map, a measurement of a refraction of an eye, and an ablation table.

Figure 2:
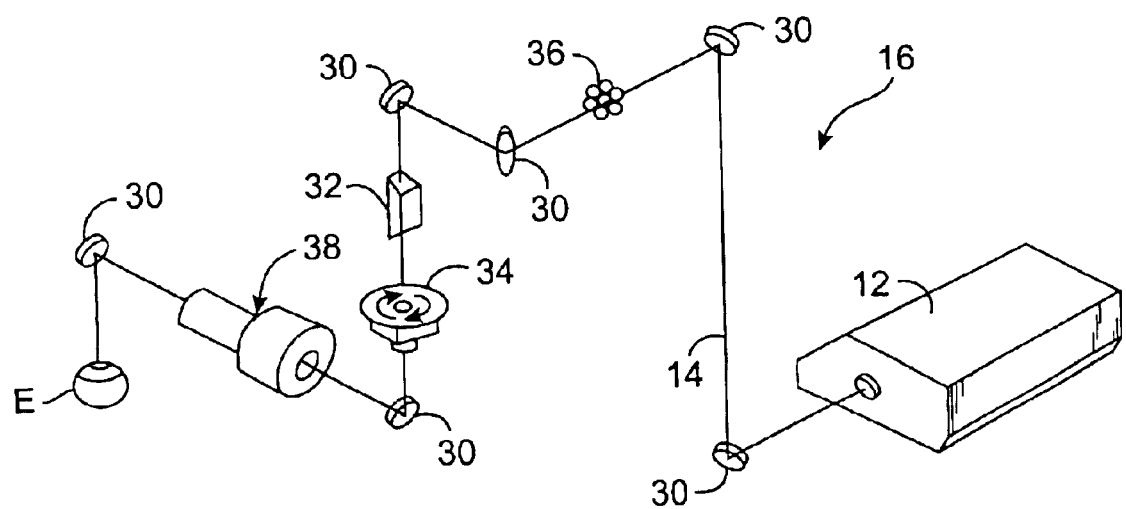
FIGS. 2 and 3 schematically illustrate a laser beam delivery system for selectively directing a laser beam onto a corneal tissue in accord with an embodiment of the present invention.

Referring now to FIG. 2, a laser beam delivery system 16 for directing a laser beam 14 at an eye 2 will often include a number of mirrors 30, as well as one or more temporal integrators 32 which may adjust (or otherwise tailor) an energy distribution across a laser beam. Laser 12 will often comprise an excimer laser as described above.

Figure 3:
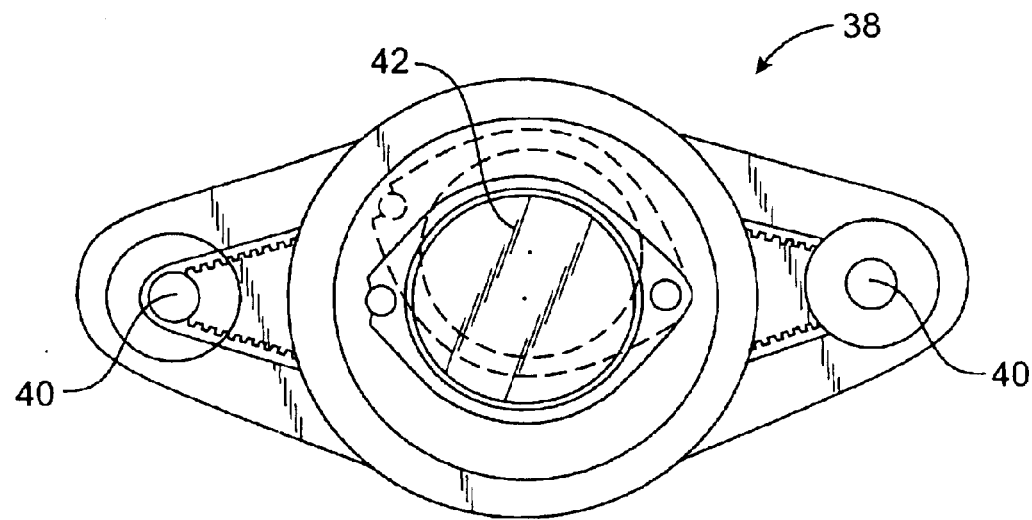

In an exemplary embodiment, a variable aperture 34 changes a diameter and/or slot width to profile laser beam 14, ideally including both a variable diameter iris and a variable width slot. A prism 36 separates laser beam 14 into a plurality of beamlets, which may partially overlap on eye 2 to smooth edges of an ablation or "crater" formed from each pulse of a laser beam. Referring now to FIGS. 2 and 3, an offset module 38 includes motors 40 which vary an angular offset of an offset lens 42, and which also change a radial orientation of an offset. Hence, offset module 38 can selectively direct laser beam 14 at a desired lateral region of a cornea. A structure and method for using a laser beam delivery system 16 and an offset module 38 are more fully described in U.S. Pat. Nos. 6,331,177; 6,203,539; 5,912,775; and 5,646,791 the full disclosures of which are incorporated herein by reference.

Figure 4:
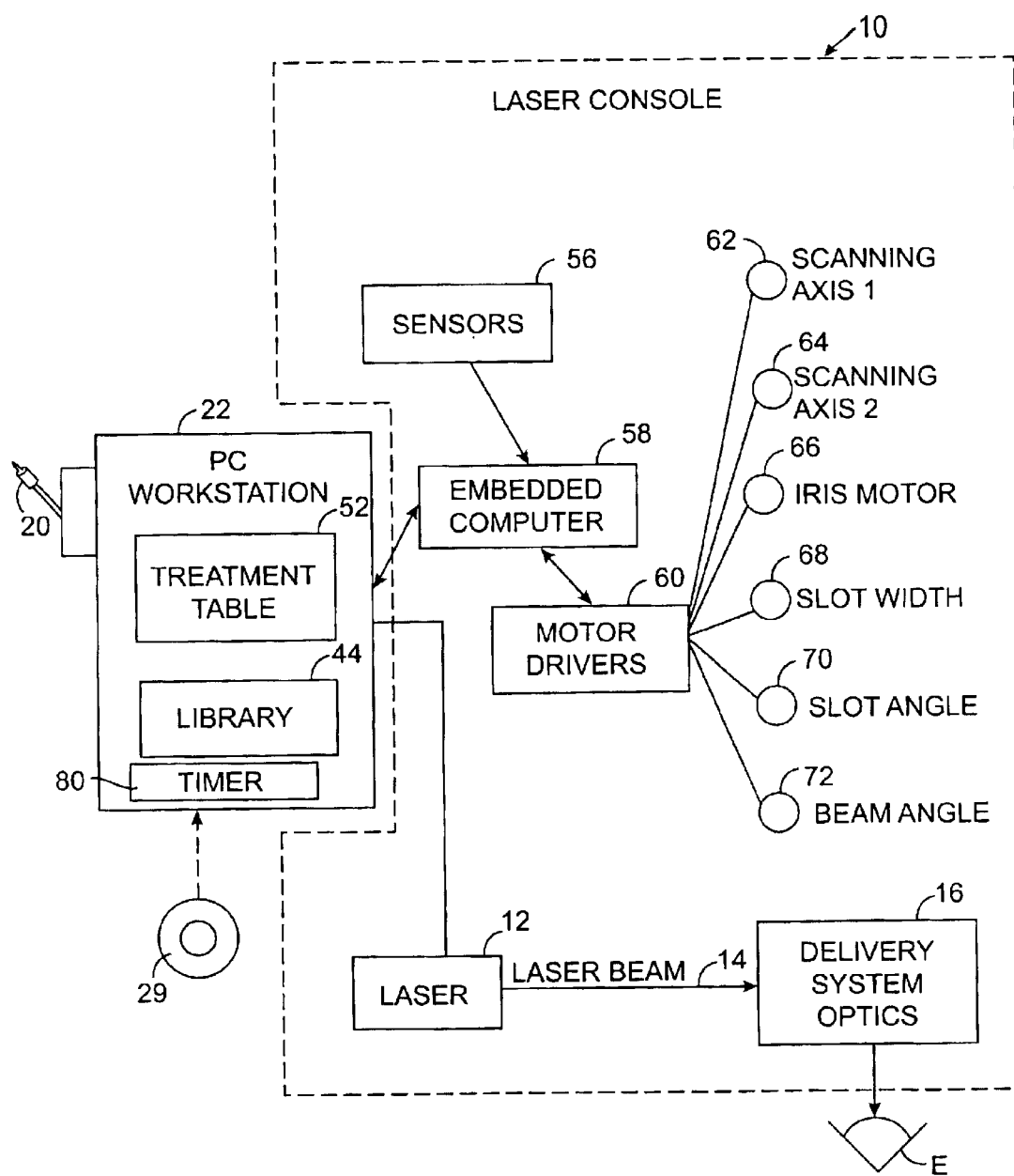
FIG. 4 is a functional block diagram illustrating a control architecture of an ablation system as in FIG. 1A in accord with an embodiment of the present invention.

Referring now to FIG. 4, a control system of a laser system 10 is schematically illustrated according to principles of the present invention. A processor 22 enables precise control of laser system 10 to sculpt a surface shape according to a laser treatment table 52. A processor 22, which generally comprises a PC workstation, makes use of a computer program stored on a tangible media 29 to generate treatment table 52. Processor 22 includes a library 44 of treatments as described in U.S. Pat. No. 6,245,059, the full disclosure of which is incorporated herein by reference. An embedded computer 58 within laser system 10 is in electronic communication with the PC workstation. Alternatively, a PC workstation may be embedded in laser system 10 and include an embedded processor card in communication with a PC workstation for directing an ophthalmic surgery.

Embedded computer 58 is in electronic communication with a plurality of sensors 56 and a plurality of motor drivers 60. Motor drivers 60 are coupled to an embedded computer 58 to vary a position and configuration of many of optical components of delivery optics 16 according to treatment table 52. For example, first and second scanning axes 62, 64 control a position of an offset lens to move several laser beamlets over a surface of a cornea. Iris motor 66 controls an overall diameter of a beam, and in some cases, a length of light transmitted through a variable width slot. Similarly a slot width driver 68 controls a width of a variable slot. Slot angle driver 70 controls rotation of a slot about its axis. Beam angle driver 72 controls beam rotation as effected by a temporal integrator as described above. A timer 80 controls a time interval between pulses of a laser treatment. Timer 80 measures a time interval from a previous pulse and generates an interrupt after a predetermined time interval has elapsed. Processor 22 issues a command for laser 12 to generate a pulse of laser beam 14 after various optical elements have been positioned to create a desired crater on eye 2 and after a measured time interval has elapsed. Treatment table 52 comprises a listing of all desired craters to be combined so as to effect a treatment therapy.

Figure 5:
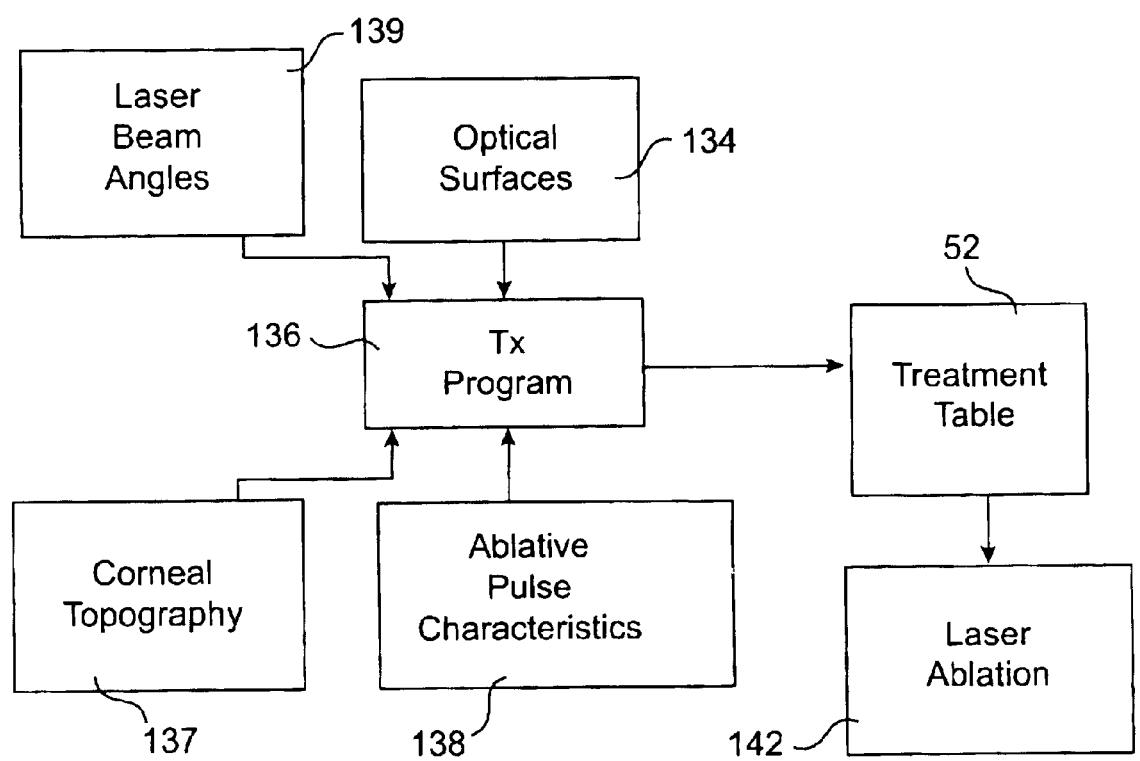
FIG. 5 is a flow chart schematically illustrating a method for determining a corneal ablation treatment program in accord with an embodiment of the present invention.

A flow chart schematically illustrating a method for determining a corneal ablation treatment plan is illustrated in FIG. 5 in accord with an embodiment of the present invention. A treatment calculation program 136 uses properties of an optical tissue surface 134, corneal topography 137, ablative pulse characteristics 138, and laser beam angles 139 to determine a treatment plan listed in a treatment table 52. Optical tissue surface 134 includes information related to optical aberrations of the eye as described above. Corneal topography 137 includes a measured shape of at least one surface of the cornea, preferably a front surface as described above. Corneal topography 137 preferably includes information locating a center of a pupil in relation to mapped corneal topography coordinates. Ablative pulse characteristics 138 include information describing a shape of tissue, or "crater" removed with a pulse of a laser beam. Local laser beam angles 139 include information describing several local angles of several rays of at least one laser beam incident on several locations of a cornea in relation to a reference axis, for example an optical axis of an eye as described above.

A treatment calculation program 136 combines information from an optical tissue surface 134 with corneal topography 137 to determine a desired shape of tissue to be removed from a surface 6 of a cornea 4 to form a desired shape 8 in surface 6. Alternatively, a desired shape of tissue to be removed from a surface 6 may be calculated from an optical tissue surface, for example from a wavefront elevation map, without using corneal topography information. A desired shape of tissue removed is preferably determined from an optical tissue surface 134 so as to remove regular (spherical and/or cylindrical) and irregular errors of optical tissues as described above. Alternatively, a desired shape of tissue to be removed may be determined so as to modify optical tissue surface 134 and leave controlled amounts of aberration, for example controlled amounts of aberrations correcting presbyopia.

By combining in a treatment plan an optical tissue surface and ablative laser pulse characteristics 138 of a particular laser system, a treatment table 52 of ablation pulse locations, sizes, shapes, and/or numbers can be developed. An exemplary method and system for preparing such an ablation table is described in co-pending U.S. patent application No. 60/189,633 filed on Mar. 14, 2000 and entitled "Generating Scanning Spot Locations for Laser Eye Surgery," the full disclosure of which is incorporated herein by reference. Sorting of individual pulses to avoid localized heating, minimize irregular ablations if the treatment program is interrupted, and the like may optionally optimize treatment table 52. Preferably, a series of pulses applied to an eye are listed in a treatment table and sorted to initially apply pulses having a small cross sectional dimension followed by pulses having a larger cross sectional dimension. Alternatively, a treatment table may be sorted to apply large diameter pulses to an eye initially followed by smaller diameter pulses, and an order of pulses may provide pulses having a random size distribution. An eye can then be treated by laser ablation 142 according to a treatment table 52.

Figure 6:
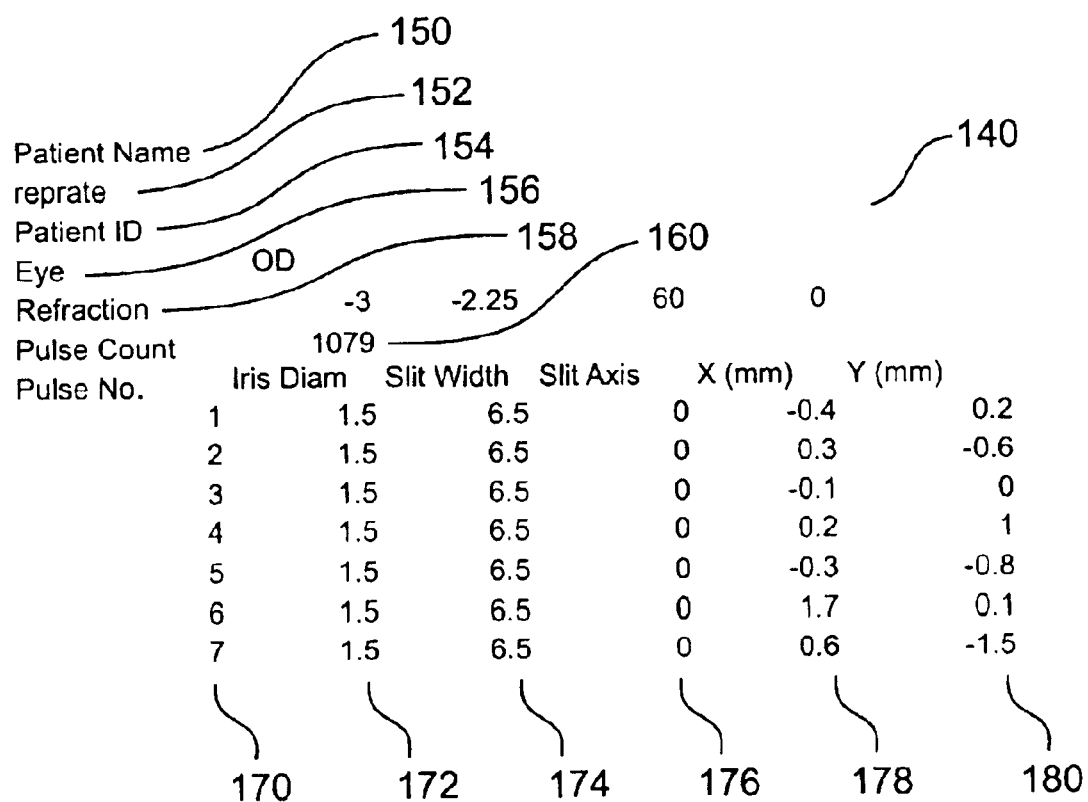
FIG. 6 illustrates a laser treatment table in accord with an embodiment the present invention.

Referring now to FIG. 6, several listings from an exemplary laser treatment table 140 are illustrated. A Patient Name 150, patient identification number (Patient ID) 154, and treated Eye 156 are listed in table 140. A repetition rate (reprate) 152 is also listed. A refraction 158 having a sphere of −3 D, a cylinder of −2.25D, an axis of 60 degrees and a vertex distance of 0 mm is listed in FIG. 6. A pulse count 160 as listed in FIG. 6 illustrates a total number of 1079 pulses applied to an eye during a treatment. Additional fields of treatment table 140 are pulse number 170, iris diameter 172, slit width 174, slit axis 176, X coordinate 178, and Y coordinate 180.

For each pulse of treatment table 140, a pulse number 170, iris diameter 172, slit width 174, slit axis 176, X coordinate 178 and Y coordinate 180 are listed. The X coordinate 178 and Y coordinate 180 list X and Y coordinates of a center of each pulse on a cornea relative to a treatment center during a treatment. An iris diameter field 172 lists a dimension across a circular iris diaphragm opening as projected onto an eye in mm for each pulse during treatment as described above. A slit width field 174 and a slit axis field 176 list a dimension across and an angle of a variable width slot opening as projected onto an eye as described above. A laser treatment table for scanning a variable width slot is described in U.S. Pat. No. 6,203,539, the full disclosure of which is incorporated herein by reference.

Figure 7:
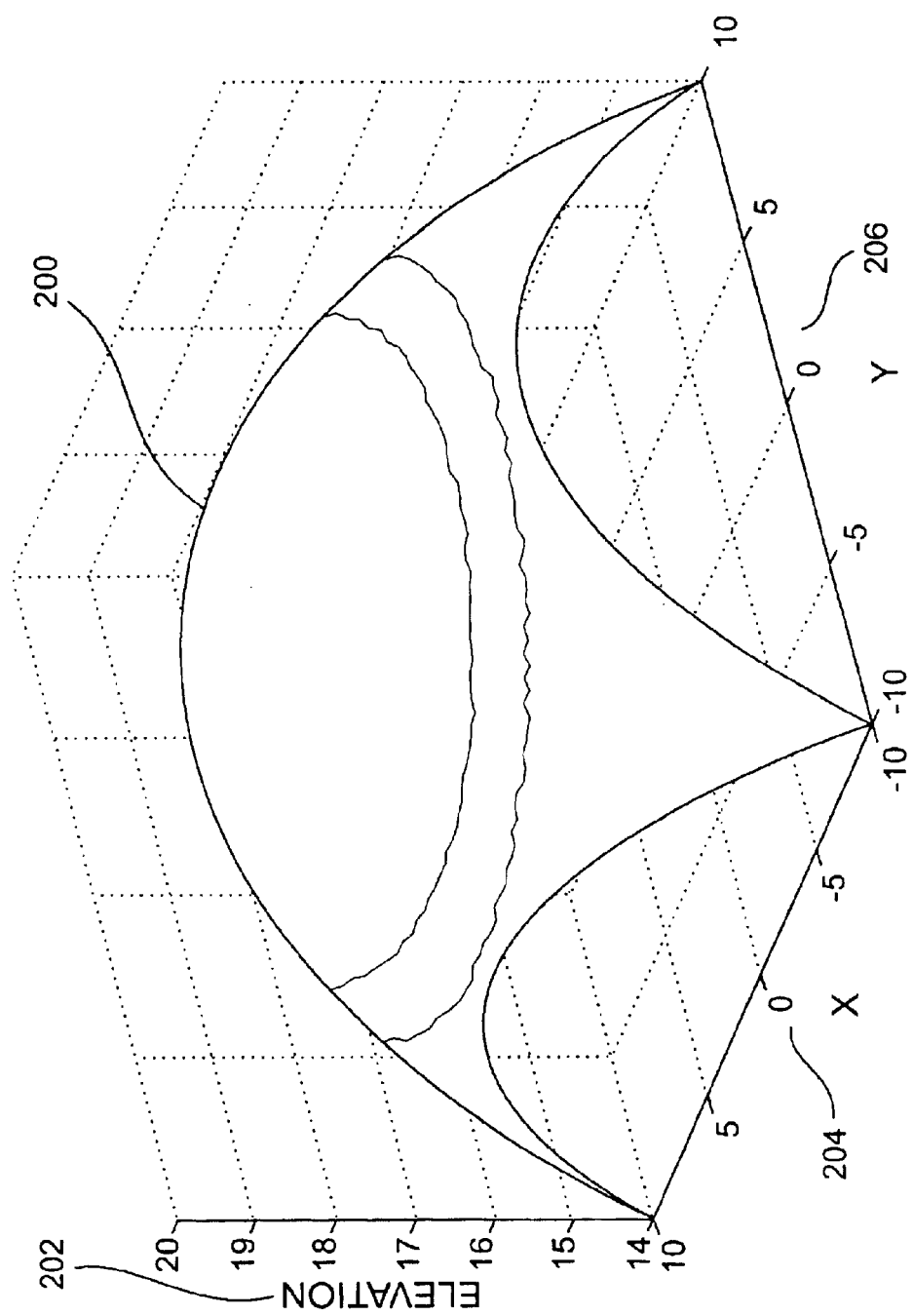
FIG. 7 illustrates a surface topography of a cornea in accord with an embodiment of the present invention.
Figure 8:
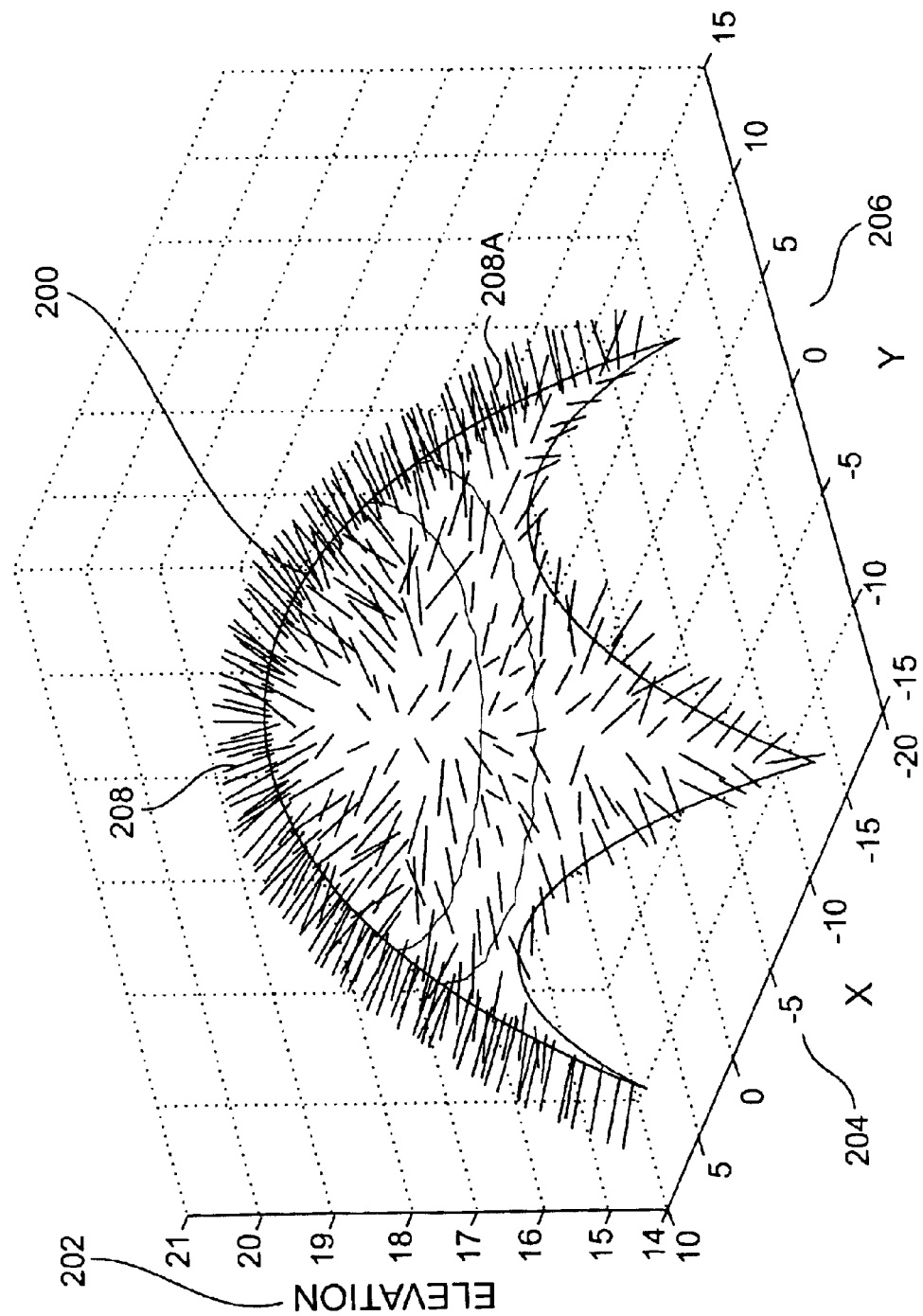
FIG. 8 illustrates local surface angles of a corneal surface topography as in FIG. 7 as surface normal vectors in accord with an embodiment of the present invention.

A map 200 of corneal surface elevation is illustrated in FIG. 7. A map 200 has an elevation 202 along a first dimension X 204 and a second dimension Y 206. For a map 200 of a corneal surface, several local surface angles are determined over a map 200 of a corneal surface as shown in FIG. 8. Several local surface angles are represented as several local surface normal vectors 208. An individual surface normal vector 208a is illustrated. A map 200 of corneal surface elevation 202 is expressed as a function Z(x,y) of first dimension X 204 and second dimension Y 206. Based on an elevation map, a surface normal vector 210 can be computed from Z(x,y) as:

$$N(x,y)=(Z_u \times Z_v)$$

where $Z_u$ and $Z_v$ are partial derivatives of the surface at point Z(x,y). A surface normal vector is preferably normalized to have a magnitude of 1. A normalized surface normal vector is expressed as $$n(x,y)=N(x,y)/\|N\|$$

Figure 8A:
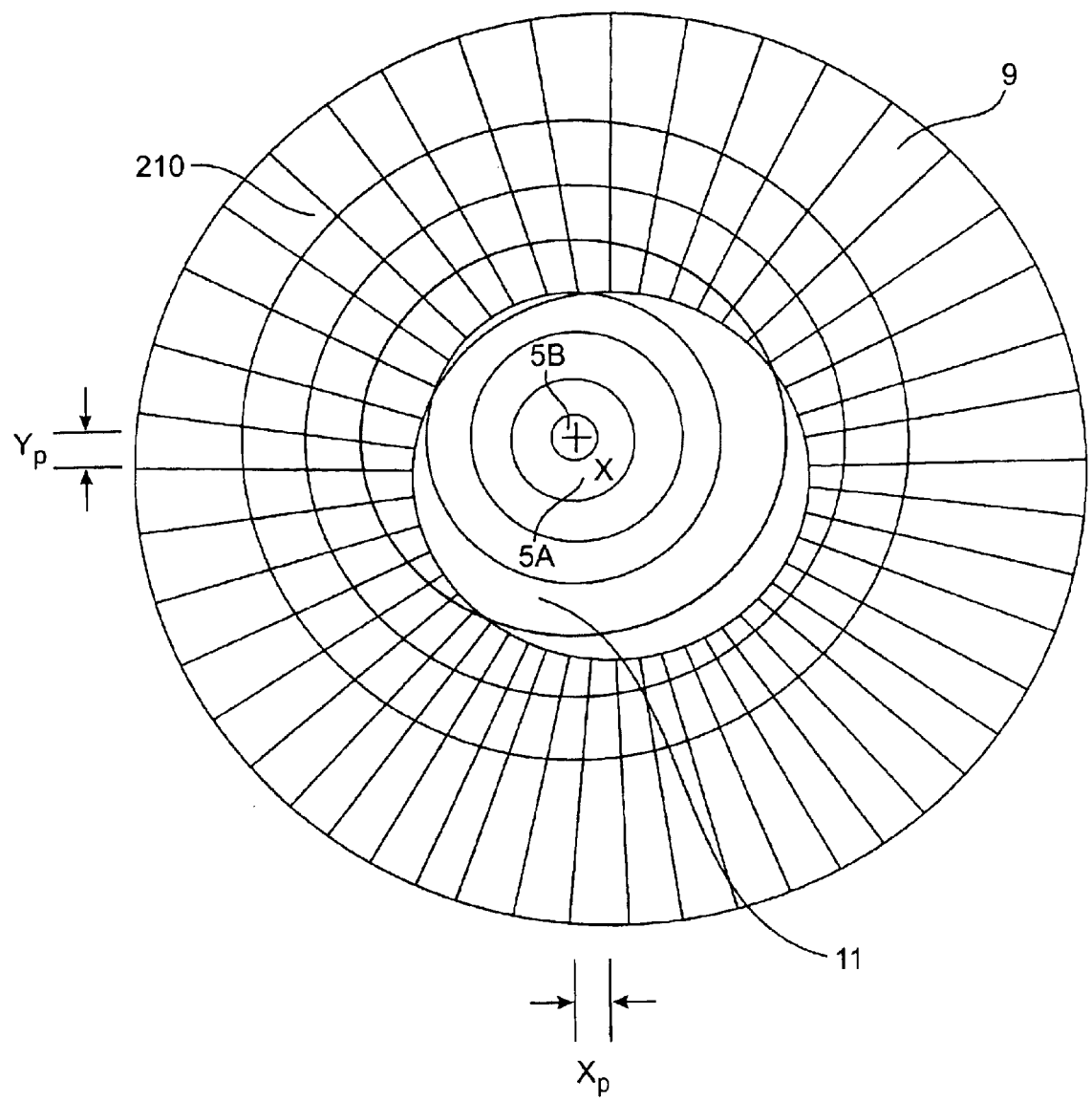
FIG. 8A illustrates a center of a pupil of an eye in relation to a center of a corneal topography measurement in accord with an embodiment of the present invention.

A measurement of a corneal topography of an eye and a pupil of an eye are illustrated in FIG. 8A. A pupil 11 is formed in an iris 9. Several rings 210 of light are reflected from a surface of a cornea during a topography measurement of a cornea. In this embodiment, a center of a topography measurement is near a apex of a cornea 5B. A center of a pupil 5A is illustrated as displaced from a apex of a cornea 5B. A center of a topography measurement is displaced from a center of a pupil by distances Xp and Yp along first and second dimensions X and Y respectively. Several commercially available corneal topography systems measure a corneal topography of an eye and a center of a pupil of an eye. For example, a Humphrey® Atlas™ Corneal Topography System is available from ZEISS HUMPHREY SYSTEMS of Dublin, Calif.

Figure 8B:
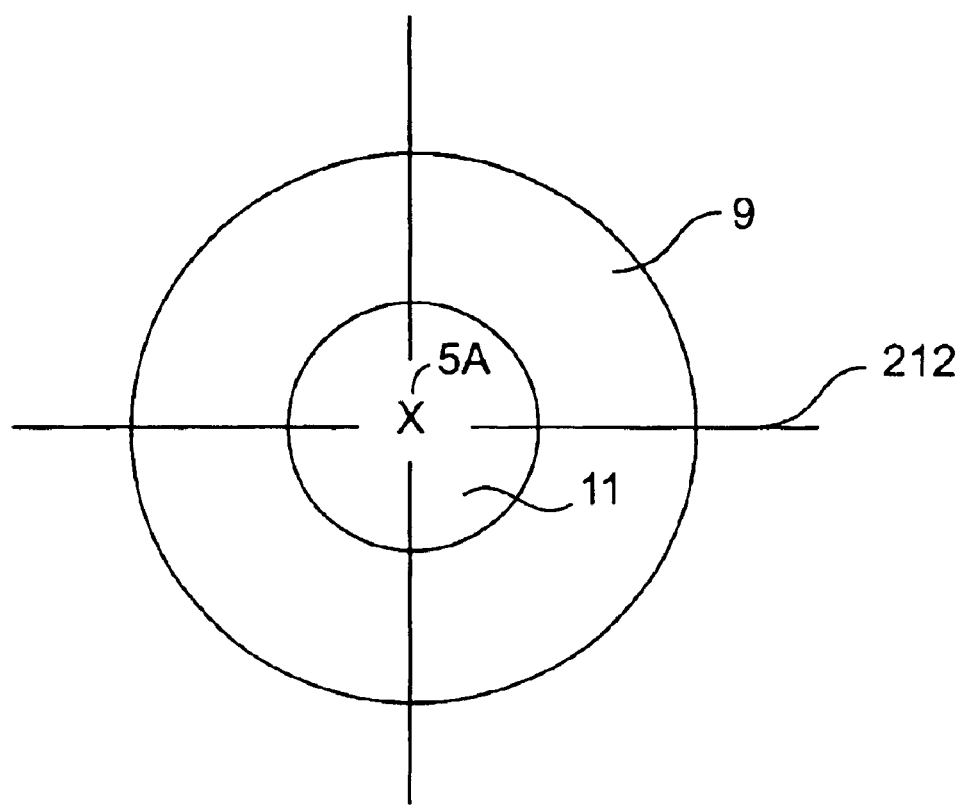
FIG. 8B illustrates a laser surgery system aligned with a center of an eye in accord with an embodiment of the present invention.

An alignment of an eye with a laser system 10 as described above is illustrated in FIG. 8B. A pupil 11 is formed in an iris 9. A reticule 212 is aligned with a center 5A of a pupil 11. In alternate embodiments, a system 10 may be aligned with any center of an eye, for example a center of a reflected image such as a first Purkinje image, a center of a dilated pupil and a center of a limbus.

Figure 9:
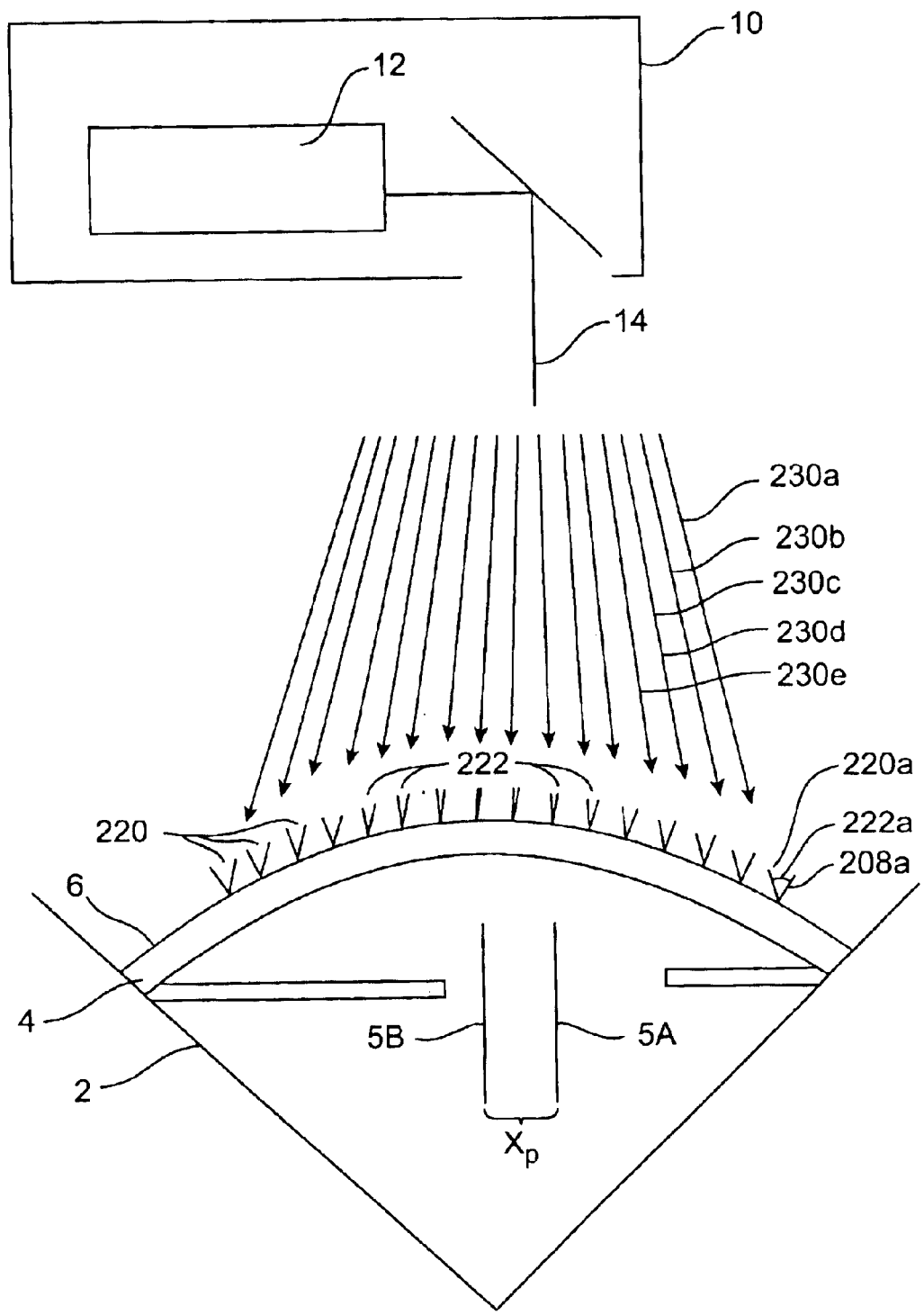
FIG. 9 illustrates angles of incidence of several rays of a laser beam incident on a surface of a cornea in accord with an embodiment of the present invention.

A surgery and an optical tissue surface measurement are centered about a pupil of an eye as illustrated in FIG. 9. A center of a pupil 5A of an eye has an associated line of sight passing through a cornea of an eye as a patient looks at a fixation target. A line of sight is also referred to as a chief ray. A wavefront measurement of an eye is centered about a pupil of an eye. A topography system generally has a central coordinate reference near an apex of a cornea 5B. A topography system may use any reference point as a coordinate center. Surface normal vectors are desirably calculated in relation to a center of a pupil. A pupil center in a topography system measurement reference system may be expressed as $(X_p, Y_p)$. A separation distance $X_p$ from an apex of a cornea 5B to a center of a pupil 5A is illustrated in FIG. 9. In a coordinate system centered about a pupil, surface normal vectors are represented as N(x',y') where $$x'=x-X_p$$

$$y'=y-Y_p.$$

A pupil-centered vector field N(x',y') is used to derive a local incident angle map $\Theta$(x',y') as a function of local position on a surface of an eye. A local incident angle map $\Theta$(x',y') describes a local angle at which a laser beam strikes a surface.

As illustrated in FIG. 9, a laser system 10 has a laser 12 that emits a laser beam 14 as described above. Several rays 230a to 230e of a laser beam 14 are illustrated. A local angle of a ray 230a of laser beam 14 incident on a cornea is illustrated as a ray normal vector 220a. A ray normal vector 220a representing an angle of a laser beam is preferably a normalized vector (i.e. has a magnitude of one). Several ray normal vectors 220 of a map of ray normal vectors are illustrated in FIG. 9. Mathematically, a map of ray normal vectors is expressed as r(x',y'). A map of ray normal vectors is readily calculated for any laser system with a ray tracing program. A map of ray normal vectors is calculated in relation to an optical axis of a laser system 10 that is aligned with a center, preferably the pupil center 5A, during surgery.

A local incident angle map $\Theta$(x',y') describes a local angle between a surface normal vector and a local angle of a laser beam incident on an eye. A local incident angle map $\Theta$(x',y') is used to determine local ablation properties of a tissue. For each of several local incident angles, a local tissue ablation property is determined. A treatment is table is generated based at least in part on a local ablation property.

Several local incident angles 222 of a local incident angle map $\Theta$(x',y') are illustrated in FIG. 9. A local incident angle 222a between a local surface normal vector 208a and a local ray normal vector 220a of a laser beam is illustrated. A local angle of incidence 222a is related to a dot product projection of a local ray normal vector 220a and a surface normal vector 208a. A local incident angle map $\Theta$(x',y') is calculated from a dot product projection of surface normal vectors 208 and several ray normal vectors 220 as $$\Theta(x',y')=\cos^{-1}[r(x',y')\cdot n(x',y')]$$

Figure 9A:
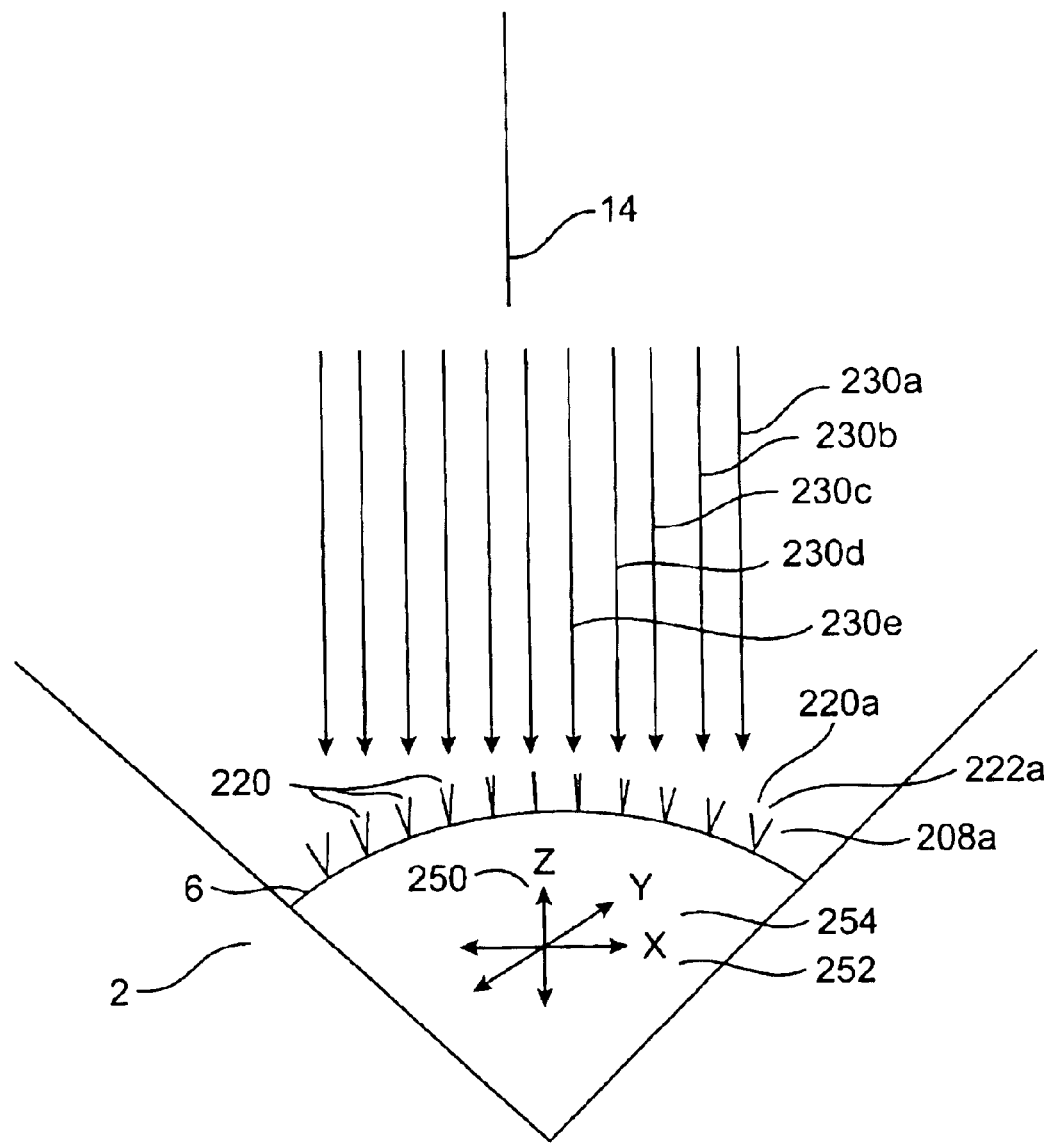
FIG. 9A illustrates angles of incidence of several parallel rays of a laser beam incident on a surface of a cornea in accord with an embodiment of the present invention.

In an embodiment illustrated in FIG. 9A, several rays 230a to 230e of a laser beam 14 are incident on a surface 6 of a cornea of an eye 2. several rays 230a to 230e of laser beam 14 are parallel. A Z axis 250 is perpendicular to a plane of X and Y coordinate references 252, 254 respectively. Z axis 250 is parallel to rays 230a to 230e. In this embodiment, a Z axis 250 is parallel to several local ray normal vectors 220 and ray normal vector 220a. A local angle of incidence 222a is related to a dot product projection of a local ray normal vector 220a and a surface normal vector 208a as described above. As ray normal vectors 220 are parallel to Z axis 250, a local angle of incidence is related to a dot product projection of Z axis 250 and a surface normal vector. A local incident angle map $\Theta$(x',y') may be calculated as $$\Theta(x',y')=\cos^{-1}(N_z(x',y')/\|N\|)$$

where $N_z$ is the z-component of the surface normal and $\|N\|$ is the magnitude of a surface normal vector.

Figure 10:
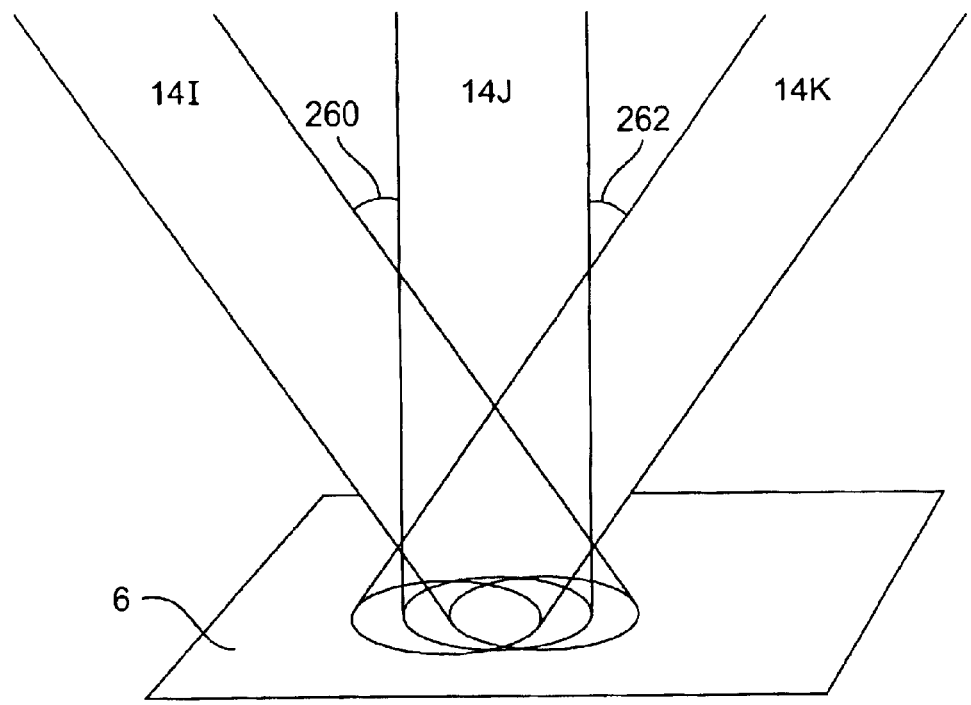
FIG. 10 illustrates laser beams simultaneously overlapping on a surface of a cornea in accord with an embodiment of the present invention.

In an embodiment illustrated in FIG. 10, a laser beam 14 as described above is divided into several smaller laser beams, for example beams 14I, 14J and 14K. Laser beams 14I, 14J and 14K overlap and are incident on a surface 6 of a cornea. Laser beams 14I and 14J are separated by an angle 260. Laser beams 14J and 14K are separated by an angle 262. Systems and methods for multiple beam laser sculpting are described in U.S. Pat. No. 6,331,177, the full disclosure of which is incorporated herein by reference.

Figure 10A:
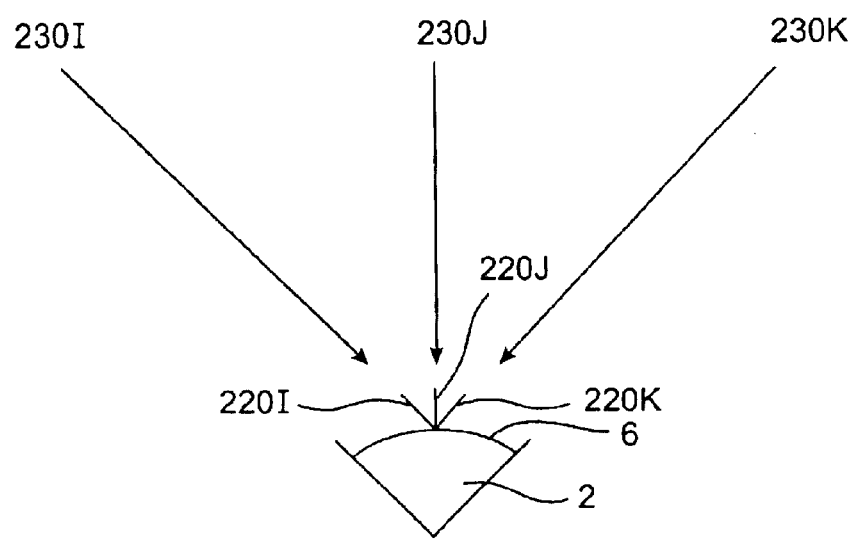
FIG. 10A illustrates angles of incidence of simultaneously overlapping rays of laser beams incident on a surface of a cornea in accord with an embodiment of the present invention.

Laser beams 14I, 14J and 14K include rays 230I, 230J and 230K incident on a common location on a surface 6 of a cornea of an eye 2 as illustrated in FIG. 10A. Ray normal vectors 220I, 220J and 220K describe an angular orientation of each of beams 14I, 14J and 14K respectively at a common location on a surface 6. An angle of incidence between each ray and a surface normal vector is calculated as described above. In some embodiments, angles 260 and 262 are small and ray normal vectors 220I, 220J and 220 K are assumed to be accurately represented by a single ray normal vector, for example ray normal vector 220J.

A local angle of incidence of a laser beam on a corneal surface is used to determine local ablation properties. An amount of light locally transmitted into a tissue is related to an angle of incidence of a laser beam. Several factors contribute to an amount of light transmitted into a tissue. Reflection of light energy from a surface is one such factor. Another factor is an effective increase in a size of surface area irradiated by a beam.

An effective fluence of a light beam applied on a surface changes with an angle of incidence of a light beam. A change in an applied fluence with a change in an angle of incidence is referred to as a cosine effect. A beam incident on a surface illuminates an increased area as an angle of incidence increases. For a fixed amount of energy along a cross sectional dimension of a laser beam, an increase in an illuminated area will decrease an amount of energy per unit area applied to a tissue. An effective fluence applied to a surface changes as a cosine of an angle of incidence. For example, a laser beam having a cross sectional diameter of 1 mm and a fluence of 160 mJ/cm$^2$ will irradiate a 1 mm cross sectional diameter of tissue with a fluence of 160 mJ/cm$^2$ when an angle of incidence is 0. However, a laser beam having a cross sectional diameter of 1 mm and oriented at 45 degrees to a surface will irradiate a cross section of tissue having a length of 1.4 mm along a first dimension and a length of 1 mm along a second dimension. An effective fluence applied to a surface will decrease to 110 mJ/cm$^2$.

Figure 11:
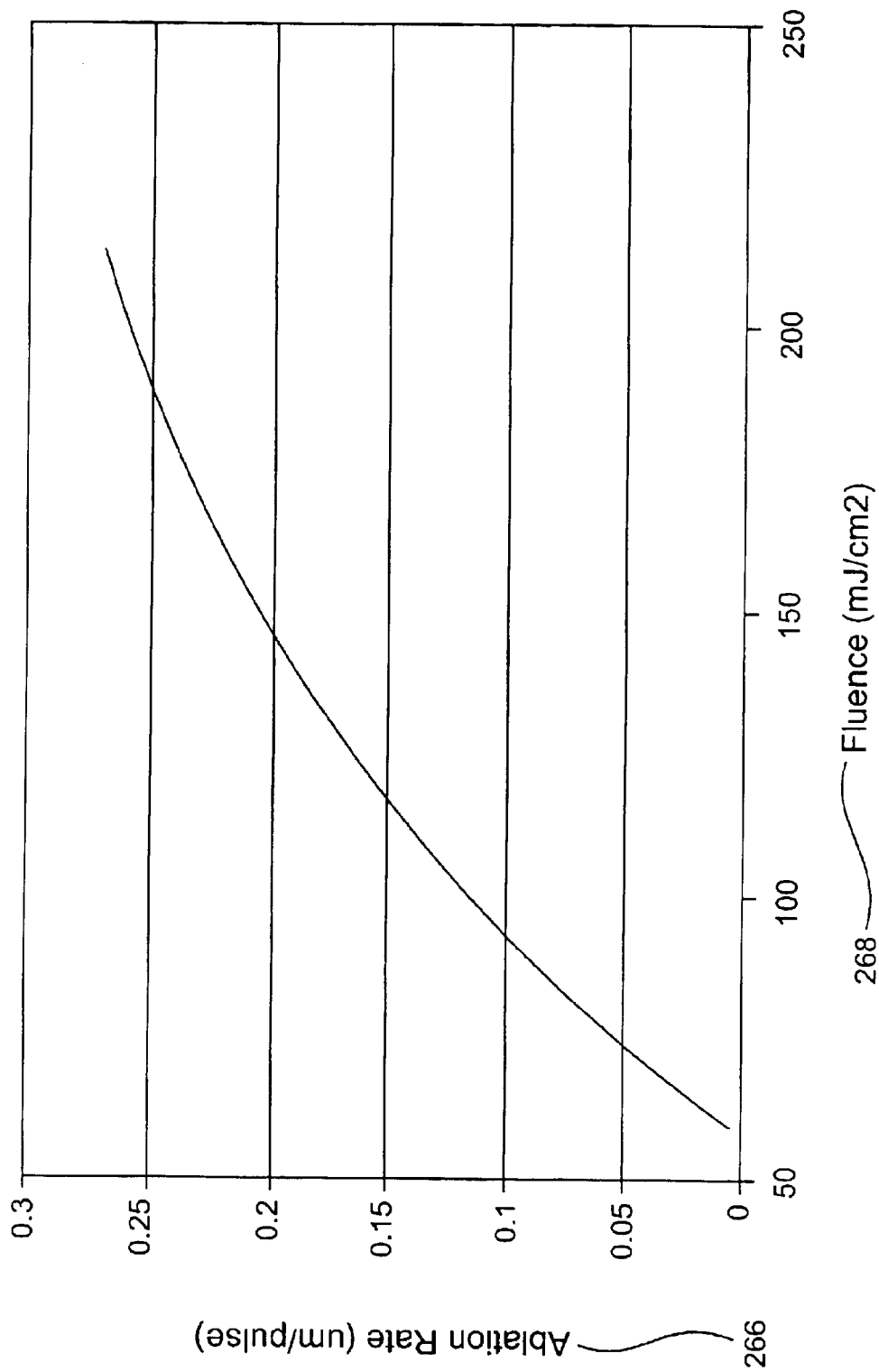
FIG. 11 illustrates an ablation rate of a corneal tissue as related to a fluence of a laser beam applied to a tissue surface.

As illustrated in FIG. 11, an amount of tissue ablated with a pulse of a laser beam depends at least in part on an amount of energy per unit area applied to a tissue. An ablation rate 266 changes with a fluence 268 of light energy applied to an eye with a pulse of a laser beam applied. At a fluence 268 of about 160 mJ/cm$^2$, an ablation rate 266 is illustrated as about 0.23 um per pulse for a laser beam at normal incidence. At a fluence 268 of 110 mJ/cm$^2$, an ablation rate 266 is illustrated as about 0.11 um per pulse for a laser beam at normal incidence. Systems and methods for measuring tissue ablation rates are known, and alternate embodiments may use a different ablation rate 266 for a similar amount of applied fluence 268.

Amounts of light energy reflected from a surface and transmitted through a surface into a tissue change with a change in an angle of incidence of a light beam. An amount of light energy transmitted into a tissue is calculated with Fresnel formulae. These formulae are known, and use an index of refraction and an angle of incidence to determine an amount of light energy penetrating into a tissue. For an excimer laser as described above polarization is random. In alternate embodiments a laser beam is polarized. A fraction of light energy transmitted into a tissue is determined by a transmissivity expressed as $$T(\theta_i)\{[(\sin 2\theta_i \sin 2\theta_t)/(\sin^2(\theta_i+\theta_t)\cos^2(\theta_i-\theta_t))]+[(\sin 2\theta_i \sin 2\theta_t)/(\sin^2(\theta_i+\theta_t))]\}/2$$

for a randomly polarized light beam, where $\theta_i$ is an angle of incidence of a light beam and $\theta_t$ is a transmitted angle of light beam. An angle of incidence $\theta_i$ of a light beam is related to a transmitted angle $\theta_t$ by Snell's law. For corneal tissue an index of refraction is about 1.377. A transmitted angle $\theta_t$ is calculated from Snell's law expressed as:

$$\sin \theta_t = \sin \theta_i/1.377$$

where $\theta_i$ is an angle of incidence of a light ray.

Figure 12:
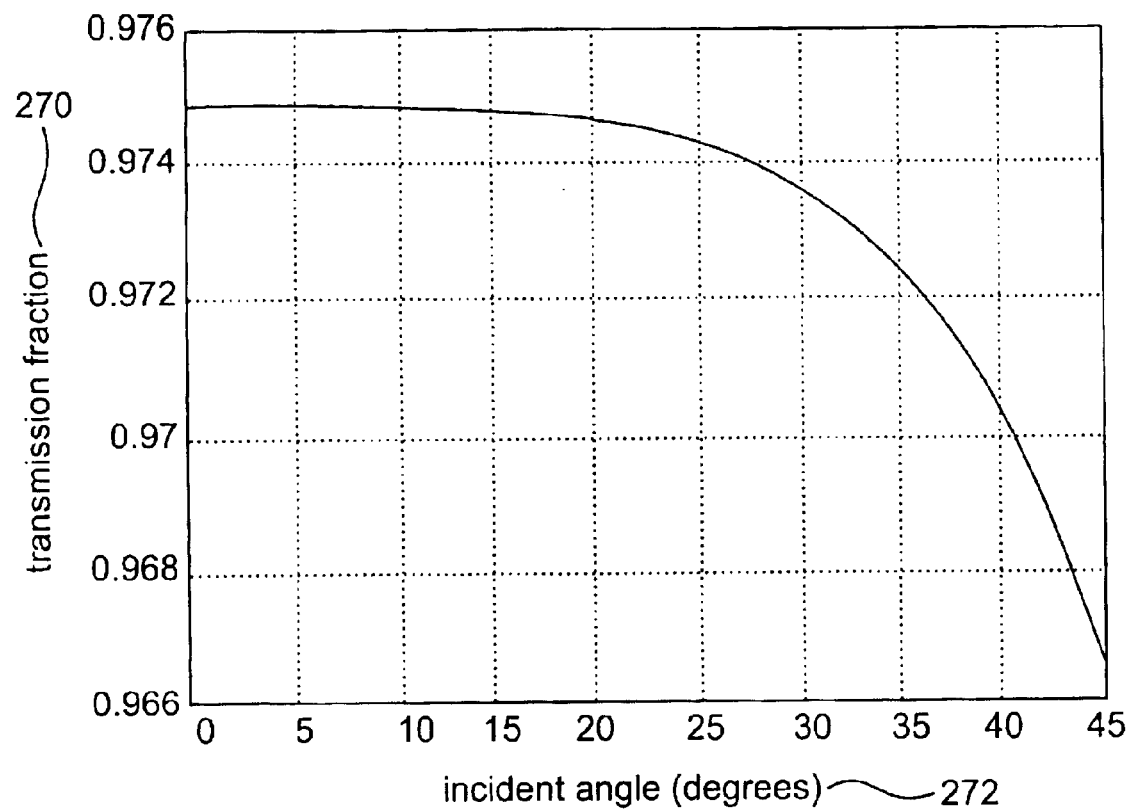
FIG. 12 illustrates a fraction of a light energy transmitted into a corneal tissue as related to an angle of incidence of a laser beam.

A fraction 270 of energy transmitted into a corneal tissue is illustrated in FIG. 12. A fraction 270 of energy transmitted into a tissue changes with an angle of incidence 272. For an angle of incidence 272 of 0, a fraction 270 of light energy transmitted into a tissue is illustrated as 0.975, about 98%. For an angle of incidence 272 of 45 degrees a fraction 270 of energy transmitted is illustrated as 0.966, about 97%.

Figure 13:
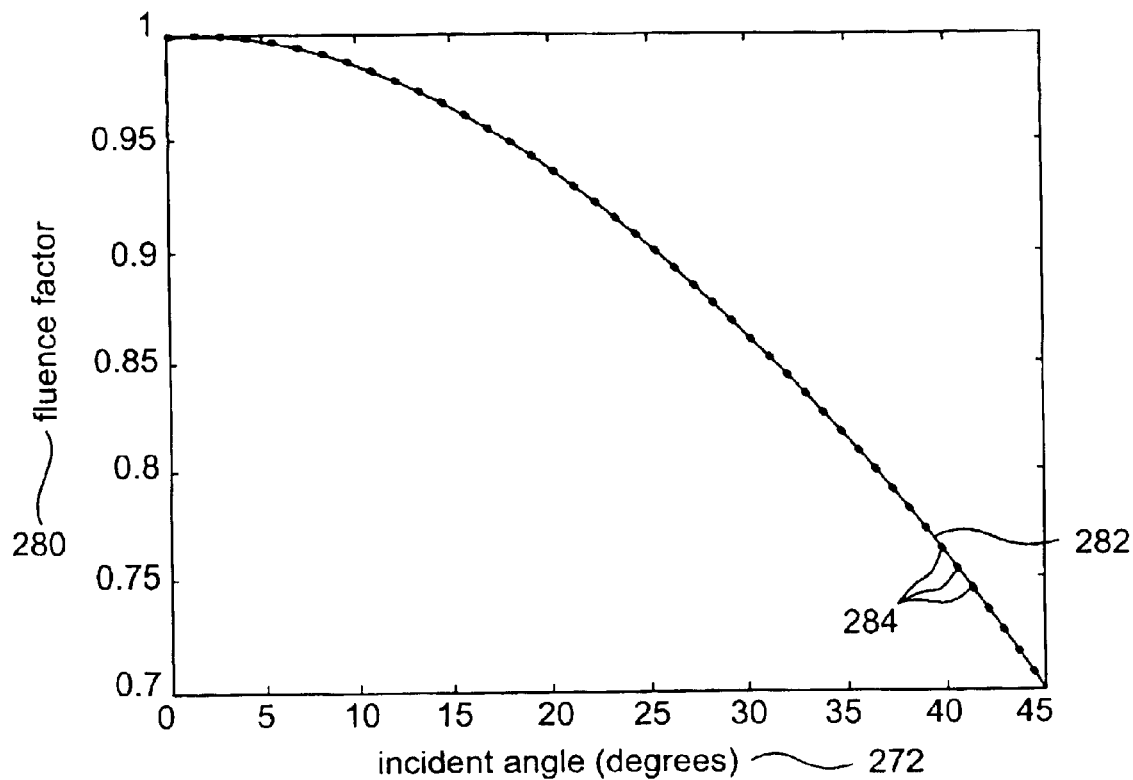
FIG. 13 illustrates a fluence factor as related to an incident angle of a laser beam in accord with an embodiment of the present invention.

A fluence factor 280 is determined for an angle of incidence 272 as illustrated in FIG. 13. A fluence factor is used to determine an applied local tissue fluence of a laser beam. A fluence factor 280 is a fraction of cross sectional beam energy transmitted through a tissue surface and varies with an incident angle 272. A fluence factor 280 includes a "cosine effect" and a transmission fraction 270 as described above. A fluence factor 280 including both a cosine projection and a transmission fraction 270 is illustrated with several dots 284. In alternate embodiments, a fluence factor may include a cosine projection of a beam onto a surface and assume reflectance to be uniform across a mapped cornea as illustrated with a solid line 282. Local tissue fluence is determined at a location by multiplying a fluence factor and a fluence of a laser beam. For a laser beam having a cross sectional fluence of 160 mJ/cm² at normal incidence to a surface and a fluence factor of 0.9 at 25 degrees, a tissue fluence is a product of 0.9 and 160 equaling 144 mJ/cm². Alternate embodiments may use a laser beam having a Gaussian energy intensity profile distribution. A local fluence may be calculated by multiplying a fluence factor by a local energy intensity at normal incidence.

For a local angle of incidence of a laser beam, a local fluence transmitted into a tissue is determined. A local tissue ablation rate is determined from a local fluence transmitted into a tissue using a tissue ablation rate as related to fluence applied at normal incidence as described above.

Figure 14:
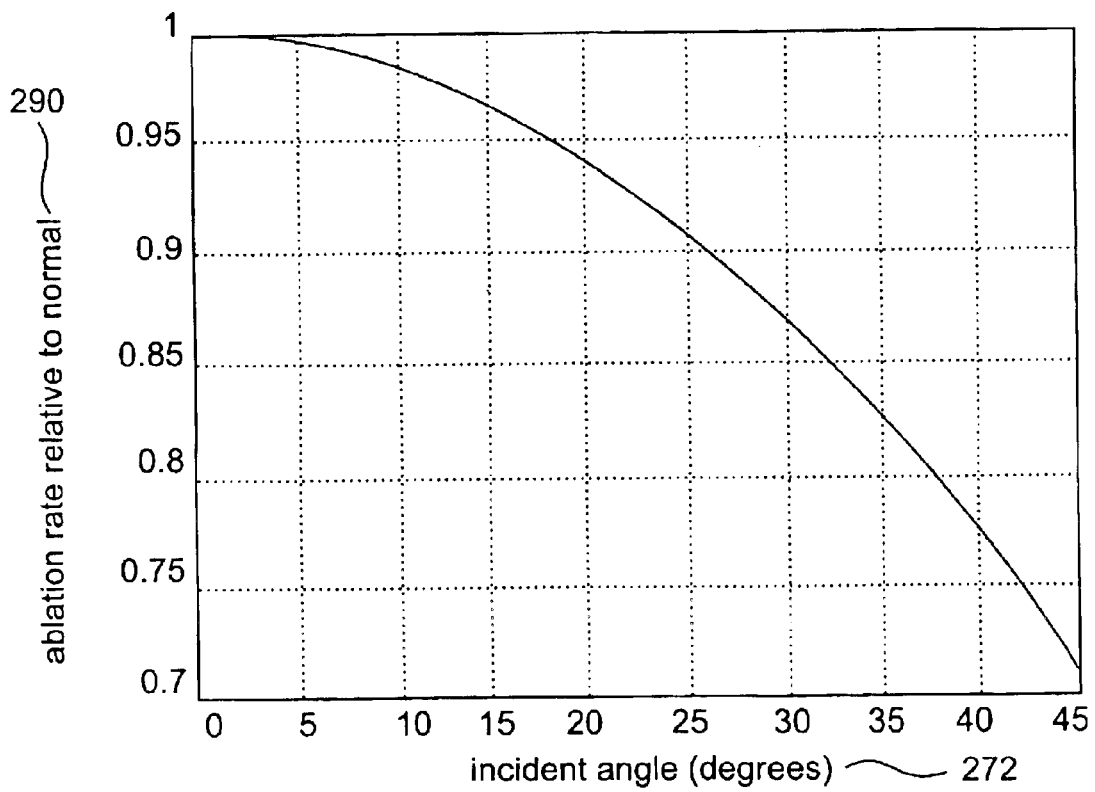
FIG. 14 illustrates an ablation rate relative to an ablation rate at normal incidence in accord with an embodiment of the present invention.

An ablation rate relative to ablation at normal incidence 290 is illustrated in FIG. 14 and varies with an incident angle 272. In an embodiment using a fluence factor, a laser beam fluence and tissue ablation rate as described above, a local tissue ablation rate relative to a tissue ablation rate at normal incidence may be determined. This local tissue ablation property may used to adjust a laser beam treatment. In alternate embodiments, a local tissue ablation rate relative to ablation at normal incidence may be accurately determined by a cosine function of an angle of incidence, for example at small angles of incidence.

Figure 15:
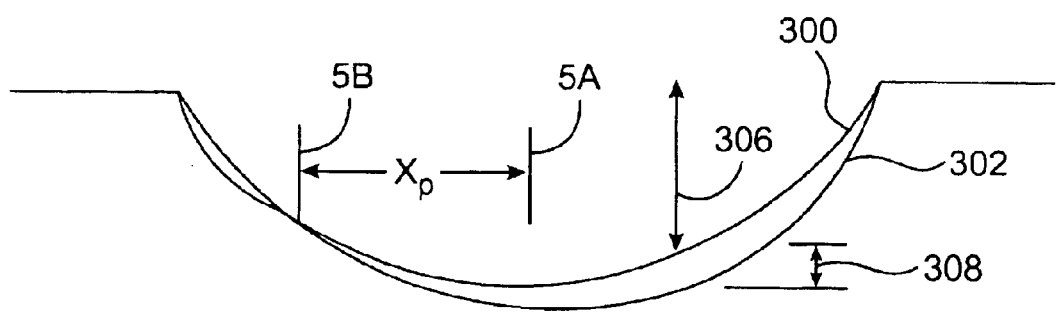
FIG. 15 illustrates a desired predetermined ablation shape as a first virtual surface warped to form a second virtual surface in accord with an embodiment of the present invention.

In an embodiment, a predetermined intended ablation shape of tissue removed from a corneal tissue is adjusted to compensate for local ablation properties as illustrated in FIG. 15. In some embodiments, an adjustment of a virtual ablation shape from a first virtual shape to a second virtual shape may be referred to as warping of an ablation target. A predetermined shape of ablation is stored in a memory of a processor as a first virtual shape 300. A local incident angle map is used to determine a map of local ablation properties, for example a map of local ablation rate relative to an ablation rate at normal incidence as described above. A first virtual shape 300 is adjusted by dividing a depth of a first virtual shape 300 by an amount of relative ablation to form a second virtual shape 302. For example, a first virtual shape 300 has a depth 306 of ablation of 10 um at a location. A map of local ablation properties determines relative ablation to be 0.9 locally. A second virtual shape 302 has a local depth of ablation of 11 um that has increased by an amount 308 of 1 um. A treatment plan is determined from a second virtual shape 302 and listed in a treatment table as described above. As a series of pulses is applied to an eye, a shape of ablated tissue matches first virtual shape 300.

Figure 16:
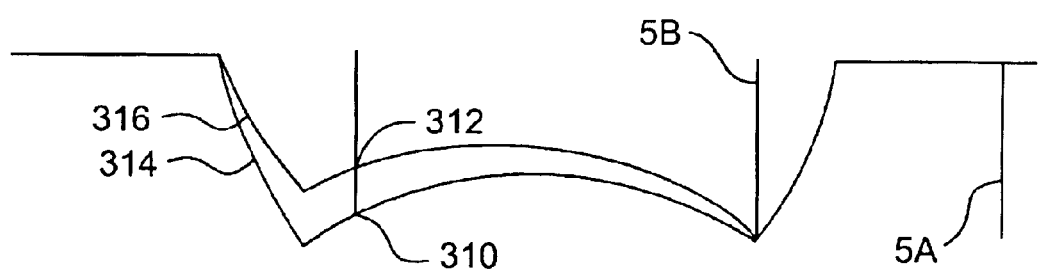
FIG. 16 illustrates a crater of material removed with a single pulse of a laser beam as a first virtual surface warped to form a second virtual surface in accord with an embodiment of the present invention.

In another embodiment, a simulated shape of material removed with each pulse of a laser beam is adjusted based on local ablation properties as illustrated in FIG. 16. At least one crater of material removed with a single pulse of a laser beam is stored in a memory of a processor as a first virtual surface 314. Systems and methods for determining shapes of tissue removed with a laser beam are described in U.S. Pat. Nos. 6,315,413 and 6,302,876, the full disclosures of which are incorporated herein by reference. During a treatment, a final ablated shape of material removed from a surface is a summation of individual craters of tissue removed with each pulse of a series of laser beam pulses. To determine a simulated shape of an ablation, each simulated crater of tissue removed in a series of pulses is adjusted by local ablation properties. As illustrated in FIG. 16, a crater described by a first virtual surface 314 is adjusted using local ablation properties to form a second virtual surface 316. Second virtual surface 316 illustrates a crater of material removed as adjusted based on local ablation properties. A center of a pupil is illustrated at 5A as described above. As illustrated for a treatment centered about a pupil, first and second virtual surfaces 314 and 316 respectively are displaced from a treatment center as may occur during a scanning treatment.

Preferably, a local fluence of light energy transmitted into a tissue is determined and a local depth of ablation determined as described above. Alternatively, a depth of ablation may be adjusted by a factor such as an ablation rate relative to an ablation rate at normal incidence as described above. A depth of ablation 310 at a location of first virtual surface 314 is decreased to a second depth of ablation 312 in second virtual surface 316 as adjusted based on local ablation properties. A center of a cornea at normal incidence to a laser beam ray is illustrated at 5B as described above. At normal incidence, a depth of first virtual surface 314 matches a depth of second virtual surface 316. To determine a predetermined shape of tissue removed by a series of laser beam pulses, several craters are adjusted based on local ablation properties and combined to determine a total shape of material removed. Each crater of a treatment is adjusted based on local ablation properties and a treatment plan is calculated and listed as treatment table as described above.

Figure 17:
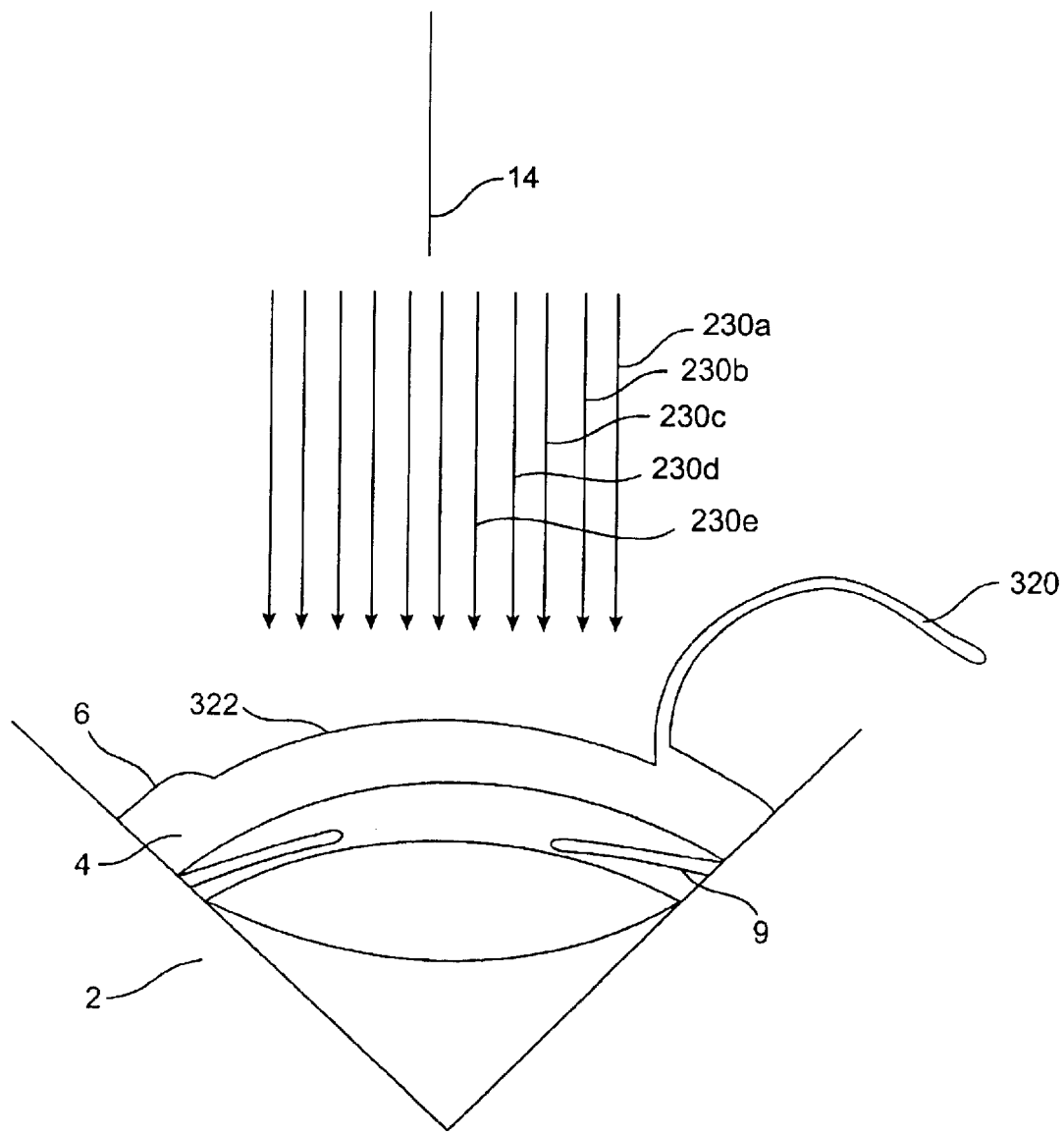
FIG. 17 illustrates a laser beam incident upon a corneal surface during a LASIK surgical procedure in accord with an embodiment of the present invention.

In an embodiment, a LASIK surgical eye procedure is performed on an eye as illustrated in FIG. 17. An eye 2 has a cornea 4. Several rays 230A–230E of a laser beam 14 are incident on a surface of a cornea as described above. Several local angles of incidence of rays of laser beam 14 are determined as described above. Local tissue ablation properties are determined at least in part in response to local incident angles as described above. A flap of corneal tissue 320 is resected from cornea 4, exposing a bed of stromal tissue 322. In a preferred embodiment, several local angles of incidence are determined before a flap of corneal tissue 320 is resected. In alternate embodiments, several local angles of incidence and local tissue ablation properties may be determined after a flap of corneal tissue 320 is resected. A laser beam treatment forms a desired ablation shape in cornea 4 as described above. After ablation, flap 320 is repositioned over a bed of stromal tissue 322.

While the above provides a complete and accurate description of specific embodiments of the invention, several changes and adaptations of the present invention may be readily made. For example, while specific reference has been made to ablating predetermined shapes based on pre-operative measurements, systems and methods of the present invention are applicable to any ablation, for example ablation based on intra-operative measurements. While specific reference has been made to correcting optical aberrations made with refractive, wavefront and topography measurements, methods and systems of the present invention can be used to ablate any desired shape in tissue based on any measurement. Therefore, the scope of the invention is limited solely by the following claims.

What is claimed is:

1. A method of treating a cornea of a patient's eye with a laser beam, the method comprising:

mapping angles between a surface of the cornea and the laser beam over a treatment area;

determining ablation properties locally across the treatment area in response to the mapped angles;

formulating a treatment plan using the ablation properties by adjusting a first virtual ablation shape to form a second virtual ablation shape, the first virtual shape representing a depth of material to be removed from the treatment area to form a desired shape, the second virtual shape being formed from the first virtual shape in response to the mapped angles and;

ablating the treatment area according to the treatment plan to form the desired shape in the surface.

2. The method of claim 1 wherein the laser beam is substantially parallel to an optical axis of the eye.

3. The method of claim 1 wherein the mapped area includes an apex of the cornea and the apex of the cornea is displaced from a center of a pupil of the eye.

4. The method of claim 3 wherein the desired shape has a center, and the center of the desired shape is aligned with the center of the pupil of the eye.

5. The method of claim 1 wherein a depth of the second virtual shape is greater than a depth of the first virtual shape.

6. The method of claim 1 wherein a depth of the second virtual shape is less than a depth of the first virtual shape.

7. The method of claim 1 wherein the desired shape is based at least in part on a result of a measurement selected from the group consisting of an aberration measurement of the eye, a refractive measurement of the eye and a topography measurement of the eye.

* * * * *